United States Patent
López Román et al.

(10) Patent No.: US 9,057,074 B2
(45) Date of Patent: Jun. 16, 2015

(54) PEDICEL SPECIFIC PROMOTER

(75) Inventors: Maria Isabel López Román, Madrid (ES); Gregorio Hueros Soto, Meco (ES); Wyatt Paul, Pont du Château (FR)

(73) Assignee: Biogemma, Paris (FR)

( * ) Notice: Subject to any disclaimer, the term of this patent is extended or adjusted under 35 U.S.C. 154(b) by 845 days.

(21) Appl. No.: 12/934,833

(22) PCT Filed: Mar. 25, 2008

(86) PCT No.: PCT/EP2008/053511
§ 371 (c)(1),
(2), (4) Date: Feb. 15, 2011

(87) PCT Pub. No.: WO2009/118039
PCT Pub. Date: Oct. 1, 2009

(65) Prior Publication Data
US 2011/0219473 A1    Sep. 8, 2011

(51) Int. Cl.
*C12N 15/82* (2006.01)
*C12N 9/50* (2006.01)

(52) U.S. Cl.
CPC ............. *C12N 15/8234* (2013.01); *C12N 9/50* (2013.01)

(58) Field of Classification Search
None
See application file for complete search history.

(56) References Cited

U.S. PATENT DOCUMENTS

| | | | |
|---|---|---|---|
| 2003/0140364 A1* | 7/2003 | Hinchey et al. | 800/278 |
| 2004/0148651 A1* | 7/2004 | Muhitch | 800/279 |
| 2007/0130645 A1 | 6/2007 | Wu et al. | |

FOREIGN PATENT DOCUMENTS

| | | |
|---|---|---|
| WO | WO 00/22144 A2 | 4/2000 |
| WO | WO-01/23594 A2 | 4/2001 |
| WO | WO-01/75071 A1 | 10/2001 |
| WO | WO-2005/118819 A1 | 12/2005 |

OTHER PUBLICATIONS

Komarnytsky, Genetic Engin 25:113-41 (2003).*
Dolferus et al., Plant Physiol 105:1075-87 (1994).*
Donald & Cashmore, EMBO J 9:1717-26 (1990).*
Kim et al., Plant Mol Biol 24:105-17 (1994).*
Wahl et al., Meth Enzymol 152:399 (1987).*

* cited by examiner

*Primary Examiner* — Medina A Ibrahim
*Assistant Examiner* — Russel Boggs
(74) *Attorney, Agent, or Firm* — Novak Druce Connolly Bove + Quigg LLP

(57) ABSTRACT

The present invention relates to controlling the expression of genes into the pedicel, more specifically in the placentochalaza cells.

14 Claims, 7 Drawing Sheets

SEQUENCE LISTING

```
<160> NUMBER OF SEQ ID NOS: 16

<210> SEQ ID NO 1
<211> LENGTH: 1556
<212> TYPE: DNA
<213> ORGANISM: Zea mays

<400> SEQUENCE: 1
caagagtttc gtagtcctgg agtattagtt ttttgtttcc ttgatcaaat accaagcaag    60
```

```
ttttgcttga aaggactaca gaaatatact actatataga ataacattgt tgtcacctgc    120
gtttacagaa ccggtcggtt tatcgaaacc gttgggccac agtttcggtt aaccaccgtt    180
ttttccaaat tcgtcctaaa ttttaaaaaa ttgaaaaaaa tataaaaacg aaaaccgtcg    240
gtaaaccgtt attttgaacg gttaaactgc tattttggat cggtaaacca ccattgtttt    300
gctggaaaac cagatttagt tccaagattg agttctagtt taggcattta gtggccagtt    360
taggcatatt agtcttgttt actgttatat gtatatgtga aaatgttata tgctatatgt    420
gaagatgatt tactgttaga tactattttt tgcccagttt aagtgctagt ttagtgctta    480
gacattacta gtgtttaact gtttatacat gacatatata tgaagatgtt ttatgtcaac    540
tatgtattgt tgttgtaaga gacatgacag acatagtatg taagcatgga gagaagattg    600
gcacgtgttt caagtgcaag tattgtagag aaacgaagag cgtagaggga catgcccaaa    660
tgcatgcaca taaactaca agcagtctag tgtgttattt ttgcttcgtc gataagtatt    720
tatttgttgt tcttgttttt cttattaatg tatctaatac cttttatata ggactacgta    780
tacagaatgg gccatatcac gatccttcca cacatgcctg agtactatta ctatgattca    840
aactgaatac gtgagtattg tgaaacatgt caacatattt gtcgtgggag aactctaaaa    900
gaacttgtat ttgagtattg tgcagtccgg tgattgattg ttgcatgaga actgaagttt    960
gtggttgcat atgaatgtcg tatgtcattt tggtgaacat atgttgtgtg aatcaattaa    1020
cataaacttt caacgcgaat tgagcaaatt ataaataaac actgacattt ttctggtttt    1080
ctataaaaaa cataaaaaat cgattcgttt tgacagaaaa ccgacagttt cggacaattt    1140
accagcggtt ttgatatttt atcgccggtt tttgcaggga aaaccgtttt aaatttgttt    1200
tggtttgaac tggccaaacc ggtcggtttt taccgggttt tagcggttta gcgacggtaa    1260
accattaccg ctgggtagcg gttttttctg ttaaaatggt ttggttaacg ttggttgtca    1320
ctgacaaatg gtcctgggcc ccacatgtca tcttcatgag gatcacatcc ctaagagtgt    1380
taataatgaa cagaatcttt tagtccaata caccgaccat actaccacca caccagcttg    1440
ccatgctgat accactgttg tgtaggatag tattgtccag ggctcgacct gtataaaagg    1500
cacacaccgg ggacgcatat cccttccacca ggagctcaca cacacatcca acagca       1556
```

<210> SEQ ID NO 2
<211> LENGTH: 1557
<212> TYPE: DNA
<213> ORGANISM: Zea mays

<400> SEQUENCE: 2

```
taacatgtgt actaacgtgt ttgctactgt ttgtgtttat agttcacaag atataaagta     60
ttgatggact aaggcagtga ggagatcaac actccaaaga agacattata aagtcatatt    120
aaagaccttt atacatgcta agagtccaac acaccaagaa gtagaagtgg gatgcaaagc    180
cacaaataaa agtgaagtta ccaaagttga gacaaaggga tgagtgaatt agaagtgtct    240 cacgatttt ggtctactca aatcgacatg gcttcaactc tgagatgtag agatttttat    300
tagctctcca aaaagttcaa gatcatcaaa atcggagctc agagctatga gttatgacta    360
taatatgaat ttgggtgtgc taaaaaaagc agcagcacag gagtagacgg tctagtgcgc    420
caaatctatt caaactgaca tggcttcaac tatgagatgt aaagagtttt attagctttc    480
caaaaagtcg aaggtcatca aaatcgaagt ttggagctaa aagttatgcc taaaatacat    540
gaagcatcat gttctgcgta agaggtccgg tgcgccaagt acgaaatgtc tggtgcgcca    600
```

| | |
|---|---|
| atttcagaag gctatcgcta acagctagta cacgtgaagg tccggtgcgc tacagaactt | 660 |
| gcttttaat gactagtttt agtttggtgc ttatatatac cacaccaccc atccatttgg | 720 |
| agatgttgga gtccaagcaa catacacata ccgagtgaag tgaggcacac ctccatagct | 780 |
| ctaaacaccc aagtacttaa tagaatcact atgtgattag cgtatgtgct ttacgaagtg | 840 |
| cttagattag ttagaccgct attgcgcttg ctctaggttg ttcctagtag attgagtgag | 900 |
| gttagaaaaa cttatacaaa cccctcggct cttgcacgag tcgttgtact tgaaatgagt | 960 |
| gggacgagag tcttgagaga ccacaccaac cgtaattgtc gtgtggctac caccgtgtac | 1020 |
| cggacggaac gaggctcgtg gcgtttcgac cggaaactcg atagtgaaga tgacgaggag | 1080 |
| catccgagag gaggccaaaa gcggagcatc atttgcacgt gaagaaagcc tacgactctc | 1140 |
| tatagagtca atcgaccgag cgtgcttggc cctcacgtgg gcttttctttt gtgtaggggt | 1200 |
| accaatgagt gttagttaaa atattgagcg gttatagata tctcggtaaa agtactgaca | 1260 |
| catcaacggg agttagtaac ataatttgct aaacttcttt tgtggtagag atagtaacac | 1320 |
| taaggtaaaa cataatttgc acattattgt tttgttattt tcatatgttt tgtttagtaa | 1380 |
| aattatttgt ggttacattg gtgagaataa taaaaaacct aatttatcct tccctgttag | 1440 |
| accgtctgta gtccctttca agggaccaga gctcggcctc tataaaggtt cacaccgggc | 1500 |
| agtcattctt tcaccacgaa cacacggccc gcgcacacat ccatcactcc atcagca | 1557 |

```
<210> SEQ ID NO 3
<211> LENGTH: 3552
<212> TYPE: DNA
<213> ORGANISM: Zea mays
<220> FEATURE:
<221> NAME/KEY: misc_feature
<222> LOCATION: (1330)..(1330)
<223> OTHER INFORMATION: n is a, c, g, or t

<400> SEQUENCE: 3
```

| | |
|---|---|
| atcgatgagc ctgaaggact ttgcttcgcg agagagtcgc ctggcttcat cagtggtgtt | 60 |
| tttgagaagg gctccgtctg atagtcggtc gataaggggt tgacgctagt cctatcgatc | 120 |
| ggttgtcgtt accaacccac aagcttgggc catagggcca ggcaacctgg tcatcagcca | 180 |
| ccttgtccaa cccttccttt gtttgaactt caccaacggt tcgtagaggt cgaaggtgaa | 240 |
| gatctcatct gggatgggct ttttccccga cgcaatggtc gatagctcgt cggcctcggc | 300 |
| gttgaaacgt atgtagctgt ggtgcagctc gaagcctttg aacttttcct ctagcttttg | 360 |
| tactttactg tagtatgtgc acatccacat gtcgtgtagc tccattgcct tcatgaccta | 420 |
| gtcgatgacc aacttggagt tgcccctaac taggagccgc tgcacaccca cctcgctcgc | 480 |
| aatccggagc ccattgacga gggcctcata ttcagcgaca ttgttggcgg aatcaaagtg | 540 |
| gaggaagatg gcgtagcgga gtttgtgccc ttaaggcgac atgaggacga cacccgtgcc | 600 |
| gcttctggtc ttgaggtagg atccgttgaa gtacatgatc cggtactctg ggtccttgat | 660 |
| tgtgggtggc tcctgcgctt cgatccattc tgcgatgaag tcggtaagag cctagaattt | 720 |
| ggtcacagtt ctagggatgt agttgatgtc gagcccactg aggttgaggg gccattttgt | 780 |
| catgcgactg gacgcatccc gattattgat gatttcacca aggggtgcca tggacaccac | 840 |
| ctgcacgaag tgtcggtcaa agaagtggat caactcccac ttggcaatga ggactgcata | 900 |
| gagcagtttc tagatctaag ggtactgtgt cttggactcc atcagcacct cactaacgaa | 960 |
| ttaaatggac ttctgcacct tgagcacgtt tccctcgtcc tccctttcca caaccacctc | 1020 |
| aacgttgacc acctgggtgg tggctgcaac atagaggagg agtgtttcac ctgggtcagg | 1080 |

```
cacgaccaag accagtggcg agctcaagaa cacattattc ggtcgagggc ctcttggatt      1140
tcaattgtct aagaaaaatg gttgctctta ttgaggaatt tgttaagggg aatacccttt      1200
tcttcgagca tagagtcgaa ttggaaatct ctatgaatct gtgtcttctg tgtgtgtatg      1260
cattgtgaag ttcccttgca ggtgatgttc tcccttgggg aggtttgccc ctaaaaaccc      1320
ttgtttcacn tcttttgcta caccacgcac accaggtgtt cgatagaatg tacaaaccag      1380
ccttctgtgc tcaaatcaac cccaacttt tccagtgggc cacatatact accaatattc       1440
ctcccacttc atatcacctt cggtctaagc caaaagatc accatatcac caattgttgc       1500
ttctccacat gagttcactc tctgcaaacc catttagtgc tatgtgatac ccttgtcttt      1560
ccaaaacccg ttccaactac ataagatcac atcctctta tccaccaata atcaatatgt       1620
gtgtcccatg tcatcctatg ttttccatgc ctcatatgcc tcatacacct catatgccta     1680
atatgtatat ggtccactcc accatgtact gacgcgagtg tgtgtcccag gtgttagcca     1740
ccacggctgc tccgatccgt cagccaagac ccagcactta tccttcacca cttccggtcc     1800
atcagcatga gcccgcatga ctttcacctc agtcgtcgat taccgtccct gtgctccaca    1860
catgcacaag ctgaccgaca ttgttgccca tacataatct cacactgtgg tcagtccact     1920
gtctaccaga gagtgctacc cgttgacaat tactcattat caactcgaat cataatggaa     1980
aagtcaacct tgtgttcgca tatttggtaa cccttaacaa tattttctc atgtagtaaa      2040 aatctctaag aattttgaa atatttcaaa gaaccaaacc aaaccaatct atccgccatt       2100
ccttgtcgta atgttggagc cactaatagc agctaaccaa ctaccacgag taaccattaa     2160
tagatgattt atgtgtaaaa taaaatcaag aaaaactttt ctaatatctc aactatcaac     2220
aaatggttcg tactgattga ttaaatatat gtaacttatg tgcattttat acgttaaata     2280
tttattctat cccaaatatt gtttcaaaat attaaaaaca aaggagtcta ctgcatttac     2340
tgagtaactg tcaactatat ttgtctcaag taataataaa agtctcaaga cttccacaac     2400
atttcaagga accaaaccta accttactat agttatgaat tgtcatagta atgttggagc    2460
ttttggtaga agacagctgg ctttaaccta aaatcatcaa tatttataat ggcttggtct    2520
acatagtcaa atcatgctaa acctctttta tcatgtcatc ataaacatat tcttccttga     2580
taaattaatt tattgcatat aactcgtgtg catttgtgcc tagtagaaaa atattatttc     2640
ccaatattca tccaaaaata tcataaatat aaaacatagg attctattgg attcattgag     2700
taaccctcaa ctacatttgt ctcatgtaat aaaatagcct taaaatttct aatacatttc     2760
aaagaactaa atccagcctt actccagcta tgattcctca tggtaatttc aaacttacta     2820
atagaagacc cccatcccta cctataccc tcaatagtca tgatgaaatt atgtacaaat      2880
tgaaatcaag ctaaatcaat tttatttcga atagtaattt ccaaacagtt aatagaagaa     2940
gcatgacccc acctataatc ctcattatac atgatggctt tatatacaaa ataaagccgt     3000
gccaaataca tttgaccaca attatgaaca tataaatata acataggat tctattggat      3060 tcattgagta accttcaact acatttgtct catgtaataa aatagtctta aaactttcaa     3120
tacatttcaa cgaactaaat ccaaccttac tccaactacg attcatcatg gtaatttga     3180 acttactaat agaagatccc caaccctgcc atatatcccc ctcaaaagtc aatgatgaga    3240
ttttgtacag aatcaaatca agcttaatca aattttattt cctaggagta attttgaaac    3300
agttaataga atatgcatga cccccaccta taatcctcat catacatgat ggctttgcat    3360
agcaaaacaa agtcatggaa aatacccttg accacaatta tgaacatatg gttccttgca    3420
```

```
agaattaaat gcgtagaatt cataggcatt tgaatctatg aatagaagtg gtatctagtg   3480
gggctataaa tagaccagct cccagcttct tttgacacaa ctcactacct tttcatcttc   3540
caagtctctg cc                                                       3552
```

<210> SEQ ID NO 4
<211> LENGTH: 46
<212> TYPE: DNA
<213> ORGANISM: Artificial
<220> FEATURE:
<223> OTHER INFORMATION: Synthetic primer

<400> SEQUENCE: 4

```
ggggacaagt ttgtacaaaa aagcaggctt atcgatgagc ctgaag                  46
```

<210> SEQ ID NO 5
<211> LENGTH: 50
<212> TYPE: DNA
<213> ORGANISM: Artificial
<220> FEATURE:
<223> OTHER INFORMATION: Synthetic primer

<400> SEQUENCE: 5

```
ggggaccact ttgtacaaga aagctgggta tggcagagac ttggaagatg              50
```

<210> SEQ ID NO 6
<211> LENGTH: 35
<212> TYPE: DNA
<213> ORGANISM: Artificial
<220> FEATURE:
<223> OTHER INFORMATION: Synthetic primer

<400> SEQUENCE: 6

```
ccatggtggc tgctgttgga tgtgtgtgtg agctc                              35
```

<210> SEQ ID NO 7
<211> LENGTH: 27
<212> TYPE: DNA
<213> ORGANISM: Artificial
<220> FEATURE:
<223> OTHER INFORMATION: Synthetic primer

<400> SEQUENCE: 7

```
ggtaccaaga gtttcgtagt cctggag                                       27
```

<210> SEQ ID NO 8
<211> LENGTH: 21
<212> TYPE: DNA
<213> ORGANISM: Artificial
<220> FEATURE:
<223> OTHER INFORMATION: Synthetic primer

<400> SEQUENCE: 8

```
gcatgcattt gggcatgtcc c                                             21
```

<210> SEQ ID NO 9
<211> LENGTH: 131
<212> TYPE: PRT
<213> ORGANISM: Lycopersicon esculentum

<400> SEQUENCE: 9

```
Ser Ser Ser Gly Asn Glu Glu Ala Ala Thr Met Ile Tyr Ser Tyr His
1               5                   10                  15

Asn Val Met Thr Gly Phe Ala Ala Arg Leu Thr Ala Glu Gln Val Lys
            20                  25                  30
```

```
Glu Met Glu Lys Ile His Gly Phe Val Ser Ala Gln Lys Gln Arg Thr
            35                  40                  45

Leu Ser Leu Asp Thr Thr His Thr Ser Ser Phe Leu Gly Leu Gln Gln
    50                  55                  60

Asn Met Gly Val Trp Lys Asp Ser Asn Tyr Gly Lys Gly Val Ile Ile
65                  70                  75                  80

Gly Val Ile Asp Thr Gly Ile Leu Pro Asp His Pro Ser Phe Ser Asp
                85                  90                  95

Val Gly Met Pro Pro Pro Ala Lys Trp Lys Gly Val Cys Glu Ser
                100                 105                 110

Asn Phe Thr Asn Lys Cys Asn Asn Lys Leu Ile Gly Ala Arg Ser Tyr
            115                 120                 125

Gln Leu Gly
    130

<210> SEQ ID NO 10
<211> LENGTH: 131
<212> TYPE: PRT
<213> ORGANISM: Lycopersicon esculentum

<400> SEQUENCE: 10

Ser Ser Ser Gly Asn Glu Glu Ala Ala Thr Met Ile Tyr Ser Tyr His
1               5                   10                  15

Asn Val Met Thr Gly Phe Ala Ala Arg Leu Thr Ala Glu Gln Val Lys
                20                  25                  30

Glu Met Glu Lys Lys His Gly Phe Val Ser Ala Gln Lys Gln Arg Ile
            35                  40                  45

Leu Ser Leu His Thr Thr His Thr Pro Ser Phe Leu Gly Leu Gln Gln
    50                  55                  60

Asn Met Gly Leu Trp Lys Asp Ser Asn Tyr Gly Lys Gly Val Ile Ile
65                  70                  75                  80

Gly Val Ile Asp Thr Gly Ile Val Pro Asp His Pro Ser Leu Ser Asp
                85                  90                  95

Val Gly Met Pro Ser Pro Pro Ala Lys Trp Lys Gly Val Cys Glu Ser
                100                 105                 110

Asn Phe Thr Asn Lys Cys Asn Asn Lys Leu Ile Gly Ala Arg Ser Tyr
            115                 120                 125

Gln Leu Ala
    130

<210> SEQ ID NO 11
<211> LENGTH: 131
<212> TYPE: PRT
<213> ORGANISM: Lycopersicon esculentum

<400> SEQUENCE: 11

Ser Ser Ser Gly Asn Glu Glu Ala Ala Thr Met Ile Tyr Ser Tyr His
1               5                   10                  15

Asn Val Met Thr Gly Phe Ala Ala Arg Leu Thr Ala Glu Gln Val Lys
                20                  25                  30

Glu Met Glu Lys Lys His Gly Phe Val Ser Ala Gln Lys Gln Arg Ile
            35                  40                  45

Leu Ser Leu His Thr Thr His Thr Pro Ser Phe Leu Gly Leu Gln Gln
    50                  55                  60

Asn Met Gly Val Trp Lys Asp Ser Asn Tyr Gly Lys Gly Val Ile Ile
65                  70                  75                  80
```

```
Gly Val Ile Asp Thr Gly Ile Ile Pro Asp His Pro Ser Phe Ser Asp
                85                  90                  95

Val Gly Met Pro Pro Pro Ala Lys Trp Lys Gly Val Cys Glu Ser
            100                 105                 110

Asn Phe Thr Asn Lys Cys Asn Asn Lys Leu Ile Gly Ala Arg Ser Tyr
            115                 120                 125

Gln Leu Gly
    130

<210> SEQ ID NO 12
<211> LENGTH: 131
<212> TYPE: PRT
<213> ORGANISM: Lycopersicon esculentum

<400> SEQUENCE: 12

Ser Ser Ser Gly Asp Glu Glu Ala Ala Ser Met Ile Tyr Ser Tyr His
1               5                   10                  15

Asn Val Met Lys Gly Phe Ala Ala Arg Leu Thr Ala Ala Gln Val Lys
            20                  25                  30

Glu Met Glu Lys Lys His Gly Phe Val Ser Ala Gln Lys Gln Arg Ile
        35                  40                  45

Phe Ser Leu His Thr Thr His Thr Pro Ser Phe Leu Gly Leu Gln Gln
50                  55                  60

Asn Met Gly Leu Trp Lys Asp Ser Asn Phe Gly Val Gly Val Ile Ile
65                  70                  75                  80

Gly Val Leu Asp Thr Gly Ile Leu Pro Asp His Pro Ser Phe Ser Asp
                85                  90                  95

Val Gly Met Pro Pro Pro Ala Lys Trp Lys Gly Val Cys Glu Ser
            100                 105                 110

Asn Phe Thr Thr Lys Cys Asn Asn Lys Leu Ile Gly Ala Arg Ser Tyr
            115                 120                 125

Gln Leu Gly
    130

<210> SEQ ID NO 13
<211> LENGTH: 131
<212> TYPE: PRT
<213> ORGANISM: Lycopersicon esculentum

<400> SEQUENCE: 13

Ser Ser Ser Gly Asp Glu Glu Ala Ala Ser Met Ile Tyr Ser Tyr His
1               5                   10                  15

Asn Val Met Lys Gly Phe Ala Ala Arg Leu Thr Ala Ala Gln Val Lys
            20                  25                  30

Glu Met Glu Lys Lys His Gly Phe Val Ser Ala Gln Lys Gln Arg Ile
        35                  40                  45

Phe Ser Leu His Thr Thr His Thr Pro Ser Phe Leu Gly Leu Gln Gln
50                  55                  60

Asn Met Gly Leu Trp Lys Asp Ser Asn Phe Gly Val Gly Val Ile Ile
65                  70                  75                  80

Gly Val Leu Asp Thr Gly Ile Leu Pro Asp His Pro Ser Phe Ser Asp
                85                  90                  95

Val Gly Met Pro Pro Pro Ala Lys Trp Lys Gly Val Cys Glu Ser
            100                 105                 110

Asn Phe Thr Thr Lys Cys Asn Asn Lys Leu Ile Gly Ala Arg Ser Tyr
            115                 120                 125
```

```
Gln Leu Gly
    130

<210> SEQ ID NO 14
<211> LENGTH: 128
<212> TYPE: PRT
<213> ORGANISM: Zea mays

<400> SEQUENCE: 14

Pro Arg Ser Thr Ser Pro Phe Ile His Thr Tyr Lys Glu Ala Ile Leu
1               5                   10                  15

Gly Phe Ala Val Asp Leu Thr Lys Asp Asp Ala Glu Tyr Val Lys Ser
            20                  25                  30

Lys Asp Gly Val Leu Met Val Tyr Lys Asp Ile Leu Leu Pro Leu Leu
        35                  40                  45

Thr Thr His Thr Pro Asp Phe Leu Ser Leu Arg Pro Asn Gly Gly Ala
    50                  55                  60

Trp Ser Ser Leu Gly Met Gly Glu Gly Ser Ile Ile Gly Leu Leu Asp
65                  70                  75                  80

Thr Gly Ile Asp Ser Ala His Ser Ser Phe Asp Asp Glu Gly Met Ser
                85                  90                  95

Ala Pro Pro Ser Arg Trp Arg Gly Ser Cys Lys Phe Ala Thr Ser Gly
            100                 105                 110

Gly His Cys Asn Lys Lys Leu Ile Gly Ala Arg Ser Leu Val Gly Gly
        115                 120                 125

<210> SEQ ID NO 15
<211> LENGTH: 131
<212> TYPE: PRT
<213> ORGANISM: Lycopersicon esculentum

<400> SEQUENCE: 15

Ser Ser Ser Gly Asn Glu Glu Ala Ala Thr Met Ile Tyr Ser Tyr His
1               5                   10                  15

Asn Val Met Thr Gly Phe Ala Ala Arg Leu Thr Ala Ser His Val Lys
            20                  25                  30

Glu Met Glu Lys Lys Arg Gly Phe Val Ser Ala Gln Lys Gln Arg Ile
        35                  40                  45

Leu Ser Leu Asp Thr Thr His Thr Pro Ser Phe Leu Gly Leu Gln Gln
    50                  55                  60

Asn Met Gly Val Trp Lys Asp Ser Asn Tyr Gly Lys Gly Val Ile Ile
65                  70                  75                  80

Gly Val Leu Asp Thr Gly Ile Leu Pro Asp His Pro Ser Phe Ser Asp
                85                  90                  95

Val Gly Met Pro Pro Pro Ala Lys Trp Lys Gly Val Cys Glu Ser
            100                 105                 110

Asn Phe Thr Asn Lys Cys Asn Asn Lys Leu Ile Gly Ala Arg Ser Tyr
        115                 120                 125

His Leu Gly
    130

<210> SEQ ID NO 16
<211> LENGTH: 131
<212> TYPE: PRT
<213> ORGANISM: Artificial Sequence
<220> FEATURE:
<223> OTHER INFORMATION: Synthetic consensus sequence
```

```
<400> SEQUENCE: 16

Ser Ser Ser Gly Asn Glu Glu Ala Ala Thr Met Ile Tyr Ser Tyr His
1               5                   10                  15

Asn Val Met Thr Gly Phe Ala Ala Arg Leu Thr Ala Glu Gln Val Lys
            20                  25                  30

Glu Met Glu Lys Lys His Gly Phe Val Ser Ala Gln Lys Gln Arg Ile
            35              40                  45

Leu Ser Leu His Thr Thr His Thr Pro Ser Phe Leu Gly Leu Gln Gln
        50              55                  60

Asn Met Gly Leu Trp Lys Asp Ser Asn Tyr Gly Lys Gly Val Ile Ile
65                  70                  75                  80

Gly Val Leu Asp Thr Gly Ile Leu Pro Asp His Pro Ser Phe Ser Asp
                85                  90                  95

Val Gly Met Pro Pro Pro Pro Ala Lys Trp Lys Gly Val Cys Glu Ser
            100             105                 110

Asn Phe Thr Asn Lys Cys Asn Asn Lys Leu Ile Gly Ala Arg Ser Tyr
            115             120                 125

Gln Leu Gly
        130
```

PEDICEL SPECIFIC PROMOTER

RELATED APPLICATIONS

Figure 1:
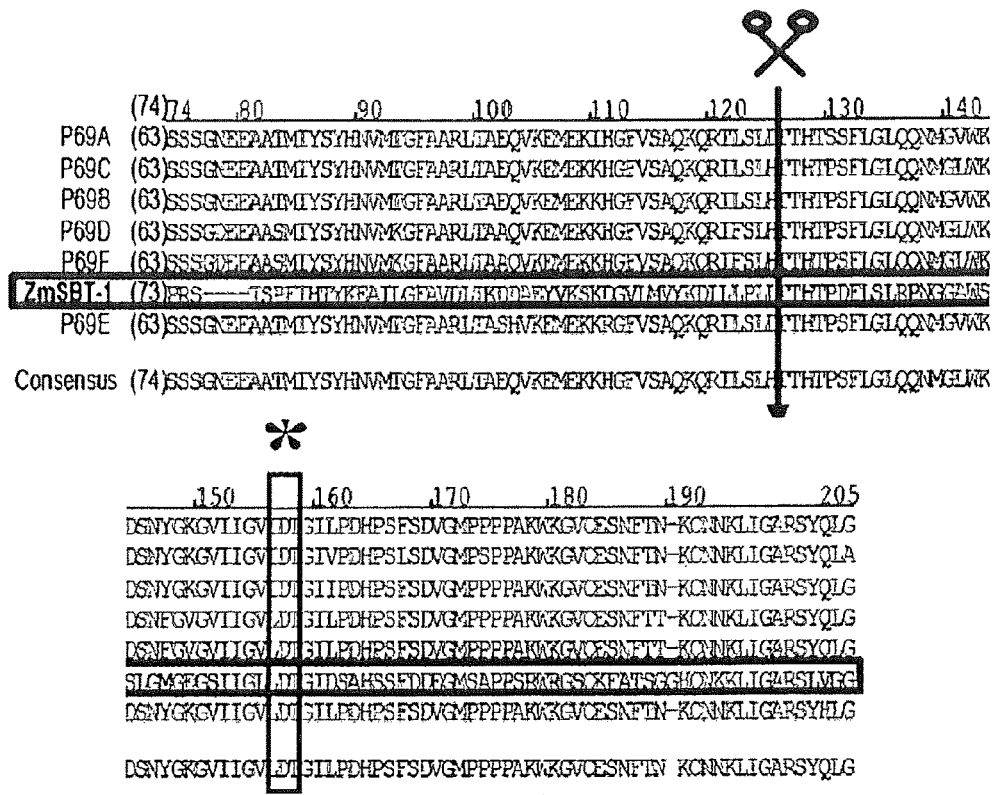

This application is a national stage application (under 35 U.S.C. §371) of PCT/EP2008/053511, filed Mar. 25, 2008.

SUBMISSION OF SEQUENCE LISTING

The Sequence Listing associated with this application is filed in electronic format via EFS-Web and hereby incorporated by reference into the specification in its entirety. The name of the text file containing the Sequence Listing is 11887_23_Seq_List_II. The size of the text file is 20 KB, and the text file was created on Jul. 17, 2013.

The present invention relates to controlling the expression of genes into the pedicel, and more specifically in the placentochalaza cells.

Subtilisin-like proteins represents an ancient family of serine proteases that are extremely widespread in living organisms. The invention is based on the identification and characterization of new Zea mays genes, ZmSBT-1 and ZmSBT-2, coding for Subtilisin-like proteases exclusively expressed in maize kernel. ZmSBT-1 was found to be expressed exclusively in the aleuron layer with a peak of accumulation around 11 DAP, while ZmSBT-2 was found to be expressed in the pedicel, and in particular in the placentochalaza within a wider developmental time frame than ZmSBT-1.

BACKGROUND ART

Cereal grains are the most important renewable resource for food, fodder and raw industrial materials for mankind. The endosperm is the main storage organ in maize seeds, nourishing the embryo while the seed develops and providing nutrients to the seedling on germination. The endosperm contains an epidermis like layer called aleurone, which is an important source of hydrolytic enzymes required for the remobilization of stored starch and protein during germination, and covers the entire perimeter of the endosperm except for the transfer cell region.

The serine proteases are one of the best characterized groups of proteolytic enzymes in higher organism. One of the largest families of this type of enzymes is represented by the subtilisin-like family (EC 3.4.21.14). All of them share a common reaction mechanism based on the catalytic triad comprising the amino acids aspartic acid, histidine and serine. The first subtilisin-like proteinase isolated from a plant source was cucumisin, which was isolated from sarcocarp of the melon fruit (Kaneda and Tominaga 1975). In the last years, several sequences related to subtilisines have been identified in different species: Lilium, Alnus, Arabidopsis, Lycopersicon, Oryza, Hordeum, Glycine, Taraxacum . . . Despite the recent advances, the current understanding of subtilase functions in plants is still very limited. However, these enzymes have been associated to a number of physiological roles in the plant cell like microsporogenesis, symbiosis, hypersensitive response, signal transduction, differentiation, senescence and protein degradation/processing.

Currently, several examples about Subtilisin-like genes implicated in plant defence are known. The P69 Subfamily in tomato, which is formed by 6 Subtilisin-like proteases (P69A, P69B, P69C, P69D, P69E and P69F), has been implied in defence against attacking pathogen (Tornero et al. 1996; Tornero et al. 1997; Jordá et al. 2000; Jordá and Vera 2000). The P69B and P69C genes do not appear to be constitutively expressed at any stage of normal plant development. Instead, they are co-ordinately and systemically induced de novo by salicylic acid treatment or following infection with the pathogen Pseudomonas syringae (Jordá et al 1999). Jordá et al. suggested that both P69B and P69C Subtilisines may play roles as active defence weapon against the attacking pathogen or alternatively, they make take part in the remodeling or reprogramming processes of the extracellular matrix, including the cell wall, that are characteristic of pathogen afficted plants (Jordá et al 2000).

As other examples of subtilisins, the SDD1 gene encodes a Subtilisin-like protease which acts as a processing protease involved in the mediation of a signal that controls the development of cell lineages that lead to guard cell formation (Berger and Altmann, 2000). Another Subtilisin-like protein, ALE1, has been involved in the formation of a cuticle on embryos and juvenile plants (Tanaka et al. 2001). The mutant phenotypes of SDD1 and ALE1 demonstrate that at least some subtilases carry out highly specific functions in plants development. Their modes of action in the regulation of the respective developmental processes are still unknown, but SDD1 and ALE1 may be required for the generation of peptide signals, which act non cell autonomously to control plant development (Von Groll et al. 2002, Tanaka et al. 2001).

DESCRIPTION OF THE INVENTION

This invention is based on the identification and molecular characterization of ZmSBT-1 and ZmSBT-2, new subtilisin-like protease genes specifically expressed during early stages of kernel development in the aleurone layer and pedicel, respectively.

The inventors demonstrated that ZmSBT-1 is a subtilisin-like gene specifically expressed in the maize aleurone cell layer. Phylogenetic analyses (not shown) showed that SDD1 (Stomatal Density and Distribution 1 of Arabidopsis thaliana) is the Subtilisin protein closest to ZmSBT-1. ALE1 (Abnormal leaf shape 1) is another Subtilisin protein of Arabidopsis thaliana that could be related to ZmSBT-1 in this phylogenetic tree.

The data reported here suggests the possibility that ZmSBT-1 is working in epidermal surfaces development of the seed, exactly in aleurone layer. ZmSBT-1 gene is specifically expressed during early stages of the aleurone layer development. Aleurone and transfer cell form the endosperm epidermis of the maize kernel, which arises after the first, centripetal, periclinal division. ZmSBT-1 may function in the production of a peptide ligand, which is required for proper differentiation of aleurone layer, as aleurone cell fate must be actively maintained throughout caryopsis development (Becraft and Asuncion Crabb, 2000, Becraft et al. 2001).

This hypothesis is supported by the early expression of ZmSBT-1 in the outer layer of endosperm before these cells acquire aleurone cell identity completely. However, aleurone marker genes expression in these intermediate cells fate suggests that outer cells are just acquiring aleurone cell identity. In accordance with the development pattern of this cell layer (Becraft and Asuncion Crabb, 2000), ZmSBT-1 transcript is expressing from ad-germinal toward ab-germinal side. With an analysis of dek1 and cr4 mutant, it was demonstrated that ZmSBT-1 expression is dependent on aleurone cell identity, and that ZmSBT-1 is located downstream of Dek1 in the aleurone identity fate pathway. By the use of in situ hybridisation and immunolocalisation assays, the ZmSBT-1 transcript and protein were found to be present in several outer endosperm cells layers of the cr4 mutant. ZmSBT-1 is not expressed in dek1 mutant, whose epidermal layer completely lacks aleurone identity; whilst it is expressed in several cell layers in the partially differentiated patches of aleurone that appear in the cr4 mutant endosperm (Winiewski et al. 2004).

The promoter sequence of ZmSBT-1 (3552 bp) has thus been obtained. Analyses of maize transgenic plants containing a Promoter ZmSBT-1::GUS construction have shown a restricted expression of this promoter to the aleurone layer. GUS signal is detected strongly in some region of aleurone after 15 DAP, and concentrated in the upper aleurone region through the first stages of the endosperm development.

In addition, GUS assays with *Arabidopsis thaliana* transgenic plants containing a Promoter ZmSBT-1::GUS construction have shown additional information about the putative ZmSBT-1 role. Firstly, GUS signal is strongly detected in younger tissues, but this expression is transient because it disappeared once the tissues have matured. In aleurone maize s similar situation happens, in which ZmSBT-1 transcript disappears when aleurone layer begins to differentiate its typical morphological characteristics.

The promoter of the ZmSBT-1 gene is a potentially useful tool to manipulate aleurone development. Molecular markers specifically expressed in this tissue or in particular regions would be a means to visualize the positional information that exist within the developing endosperm. The comparison of the expression patterns of such molecular markers in wild type and developmental mutants would provide additional insight in the defect of the mutant and hence the developmental steps in the wild type.

As demonstrated by the inventors, ZmSBT-2, like other Subtilisines, has highly conserved structural features formed by four domains: A signal peptide, a linker region, a C-terminal peptide and an active mature enzyme. The distribution of ZmSBT-2 expression pattern was different from the one of ZmSBT-1. ZmSBT-2 transcript and protein localize exclusively at the placentochalaza cells of the kernel, within a wider developmental time frame than ZmSBT-1. ZmSBT-2 gene opens new hypothesis about the function that these new subtilisines genes play in maize endosperm.

The inventors demonstrated that ZmSBT-2 is a gene specifically expressed in the pedicel, more particularly in the placentochalaza region, in which several defence proteins have been identified (Balandín et al. 2005, Serna et al. 2001). In particular, the mature BETL2 protein preferentially accumulates in the placentochalaza region, where it might contribute to form an anti-pathogen barrier (Serna et al 2001).

The present invention relates to an isolated nucleic acid molecule having promoter activity specific to the pedicel that comprises a DNA sequence selected from the group consisting of:

a) a sequence as depicted in SEQ ID NO 1 or SEQ ID NO 2;
b) a fragment of a sequence as defined in (a), wherein said sequence has promoter activity specific to the pedicel;
c) a sequence that has at least 70% sequence identity with a sequence as defined in (a), wherein said sequence has promoter activity specific to the pedicel;
d) a sequence hybridizing with the complementary strand of a sequence as defined in (a) and/or (b) under stringent conditions, wherein said sequence has promoter activity specific to the pedicel.

Preferably, the nucleic acid molecule of the invention is specific to the placentochalaza cells.

Particularly, the nucleic acid molecule according to the invention enables expression of a nucleic sequence of interest (promoter activity), specifically in the pedicel, more particularly in the placentochalaza cells. Advantageously, this promoter activity happens before the double fertilization.

"Promoter activity specific to a given tissue" means, as used in the present invention, that the promoter is predominantly expressed in said given tissue, and preferably exclusively expressed in said given tissue.

"The placentochalaza cells" are parts of the pedicel, located near the filial tissues. These cells are involved in particular in nutriments transport.

The nucleotide sequences according to the invention may be prepared by chemical synthesis, or by mixed methods including the chemical or enzymatic modification of sequences obtained by screening banks. By reference to these promoter sequences, a "fragment" denotes a sequence, particularly a DNA sequence, which has a reduced length with regard to said sequence of reference.

A fragment, according to the invention, has promoter activity specific to the pedicel, and contains at least 500, 700, 1000, or 1200 consecutives nucleotides of SEQ ID NO 1 or SEQ ID NO 2.

A nucleic acid molecule "hybridizes" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., 1989).

Such an hybridizing sequence has promoter activity specific to the pedicel according to the invention, preferentially specific to the placentochalaza cells, and contains at least 500, 700, 1000, or 1200 nucleotides.

The invention also encompasses modifications of the DNA sequences as depicted in SEQ ID NO 1 or SEQ ID NO 2, if the nucleic sequence remains capable of driving pedicel specific expression of a gene.

"Homologous nucleic acid sequence", or "homologous DNA sequence", means any nucleic acid sequence which differs from any of the sequence SEQ ID NO 1 or SEQ ID NO 2 by a substitution, deletion and/or insertion of one or more nucleotides at positions such that these homologous nucleic acid sequences preserve the specificity property of promoters of sequences SEQ ID NO 1 or SEQ ID NO 2.

Preferably such a homologous nucleic acid sequence is at least 70% identical to one of the sequences SEQ ID NO 1 or SEQ ID NO 2, preferably at least 85% identical, more preferably at least 90, 91, 95, 98, 99.9% identical. Also preferably, the degree of identity is defined by comparison with the entire sequence of reference, SEQ ID NO 1 or SEQ ID NO 2.

Homology is generally determined using a sequence analysis software (for example, the Sequence Analysis Software package of the Genetics Computer Group, University of Wisconsin Biotechnology Center, 1710 University Avenue, Madison, Wis. 53705). Similar nucleotide sequences are aligned in order to obtain the maximum degree of homology (i.e. identity). To this end, it may be necessary to artificially introduce gaps in the sequence. Once the optimum alignment has been achieved, the degree of homology (i.e. identity) is established by recording all the positions for which the nucleotides of the two compared sequences are identical, with respect to the total number of positions.

In a preferential manner such a homologous nucleic acid sequence specifically hybridizes to a sequence which is complementary to the sequences SEQ ID NO 1 or SEQ ID NO 2 under stringent conditions. The parameters defining the stringency conditions depend on the temperature at which 50% of the paired strands separate (Tm).

For sequences comprising more than 30 bases, Tm is defined by the equation: Tm=81.5+0.41 (% G+C)+16.6 Log (concentration in cations)−0.63 (% formamide)−(600/number of bases) (Sambrook et al., 1989).

For sequences shorter than 30 bases, Tm is defined by the equation: Tm=4(G+C)+2(A+T).

Under appropriate stringency conditions, in which non-specific (aspecific) sequences do not hybridize, the temperature of hybridization is approximately between 5 and 30° C., preferably between 5 and 10° C. below Tm and hybridization buffers used are preferably solutions of higher ionic force like a solution 6×SSC for example.

The nucleic acid molecules having promoter activity specific to the pedicel according to the invention can be isolated from various plant species, notably angiosperm plants, monocotyledons or dicotyledons and are preferably nucleic acid molecules isolated from a plant selected from the group consisting of maize, teosintes, rice, sorghum, wheat, barley, rye, pea, and sugar cane. Still preferably, the plant is maize.

It is possible for the person skilled in the art to isolate with the help of promoter sequences of the invention, corresponding genes from other species ("orthologous" genes).

This can be done by conventional techniques known in the art, for example, by using a promoter sequence depicted in any one of SEQ ID NO 1 or SEQ ID NO 2 as a hybridization probe or by designing appropriate PCR primers.

It is preferable to start with coding DNA sequences or protein sequences via TBLASTN queries. The approach used to isolate rice promoters, for example, is to use the Protein sequence of maize, do a TBLASTN with this sequence against Rice ESTs, then use this EST to find the genomic sequence or directly use TBLASTN against the rice genome sequence.

It is then possible to isolate the corresponding promoter region by conventional techniques and test it for its expression pattern by known techniques (e.g. reporter gene analysis).

Another object of the present invention is a nucleotide construction, referred to as an expression cassette, comprising a nucleic acid molecule having promoter activity specific to the pedicel as defined above, operatively linked to at least one nucleic sequence of interest.

"Operatively linked" refers to functional linkage between a nucleic acid molecule having promoter activity according to the invention and the nucleic sequence of interest.

The nucleic sequence of interest can be of a heterologous origin.

The nucleic sequence of interest can be placed in the sense or antisense orientation.

According to an embodiment, the nucleic sequence of interest may be selected from the group consisting of a sequence that encode a peptide or a protein, an antisense RNA sequence, a sense RNA sequence, both a sense and antisense RNA sequence (RNAi sequence) and/or a ribozyme.

Preferentially, the nucleic sequence of interest is a sequence that codes for a protein or for a peptide.

The nucleic sequence of interest can in particular code for a protein involved in the development of the embryo and/or of the endosperm, the determination of seed size and/or quality (e.g. MRP1 or Ferretin (Lobreaux S. et al. 1992)), cell growth (proteins regulating cell division including cytokinin or auxin genes, e.g. ipt (Zhang et al. 1995), the flow of nutrients or nutrient transfer (transporters (Bolchi A. et al. 1999)), proteins involved in fatty acids metabolism. The nucleic sequence of interest may also encode an enzyme involved in sugar metabolism such as invertases (e.g. incW2 (Taliercio E W et al. 1999)), sucrose synthases (e.g. Sh1), the saccharose phosphate synthase, saccharose synthase, UDP-Glucose pyrophosphorylase, ADP-glucose pyrophosphorylase (Thomas W. Greene et al. 1998), starch branching enzyme (Ming Gao et al. 1997) or the starch synthase (Mary E. Knight et al. 1998). The nucleic sequence of interest could also code for a hexokinase as the one described by Jang et al. (1997) in order to improve grain filling. The nucleic sequence of interest may additionally code for a protein that is involved in amino acids transfer, such as a methionine permease or a lysine permease, or a sulphur transporter etc. It can also code for a toxic protein such as Barnase, for a protein activating or inhibiting other genes, such as transcriptional regulators including transactivators modified to act as dominant activators or repressors of transcription (e.g. fusions to the engrailed domain (Poole et al., 1985) or co-repressors for example), or for a protein improving resistance to pathogens (e.g. BAP2, MRP1).

Preferably, said nucleic sequence of interest encodes a protein selected from:

a protein whose specific expression in the pedicel, makes it possible to increase nutrient uptake and thus seed size and/or quality. Examples of such a protein include an invertase like Incw2 or like Ivr1 (EP 0 442 592), a sucrose synthase like Sh1 (WO 02/067662) or any transporters of sugar and nitrogen or a MRP1 protein etc. Anderson et al., 2002, have shown that the repression of soluble and insoluble invertase by drought during the early stage of development of the young ovaries is responsible of seed abortion. The described pedicel promoter may thus be advantageously used to drive the expression of an invertase to produce a plant with a reduced abortion rate when subjected to water stress. One can also use this promoter to drive expression of the glutamine synthase of maize shown to be expressed in the pedicel by Muhitch et al., 1989, or the seed-specific thioredoxin ZmTRXh1 described by Santandrea et al., 2002.

a protein that improves resistance to pathogens; examples of such a protein include a BAP Protein (Basal Layer Antifungal Protein) (Serna et al., 2001), or anti-fungal peptides, or a MRP1 protein or a protein that encodes an oxalate oxidase (WO 92/15685) or a protein that encodes a chitinase (WO 92/01792 or U.S. Pat. No. 5,446,138) or a protein that encodes a glucanase (WO 93/02197) etc.

A protein that "improves resistance to pathogens" or "a protein improving resistance to pathogens" means a protein that, when expressed in a plant or a part of a plant, confers or improves resistance to pathogens to said plant, or part thereof. Said transformed plant has a better resistance to pathogens than the non-transformed plant (wild-type).

Preferably the ZmSBT2 promoter may be used to drives the expression of pathogene related protein or peptide. This promoter may also be advantageously used to drives the expression of proteins which interferes with the replications of virus or fungi, for improving pathogen tolerance of the plant to these virus or fungi.

Pathogens of the invention include, but are not limited to, viruses or viroids, bacteria, insects, nematodes, fungi, and the like, such as *Fusarium* species (notably *Fusarium moniliforme, Fusarium graminearum*), *Sclerotinia sclerotiorum*, *Phoma*, Corn root worm, *Aphis gossypii*. For maize, this would include especially ear mold fungal pathogens, such as *Fusarium monoliforme*.

Assays that measure resistance to pathogen are commonly known in the art, as are methods to quantitate disease resistance in plants following pathogen infection. Such techniques notably include, measuring over time, the average lesion diameter, the pathogen biomass, and the overall percentage of decayed plant tissues.

This promoter may be used to drive the expression of enzymes of the hormone biosynthesis or degradation pathways, more specifically of the abssicic acid or cytokinins pathways. One can also use this promoter to drive the expression of an antibody specific to a hormone to reduce the rate of this hormone in this compartment. These antibodies can be monoclonal antibodies, polyclonal antibodies or synthetic antibodies as well as fragments of antibodies, such as Fab, Fv or scFv fragments etc. Techniques for producing such antibodies are classical methods well known by the one skilled in the art.

The nucleic sequence of interest can also be associated with other regulating elements such as transcription termination sequences (terminators). By way of examples of such sequences, it is possible to cite the polyA 35S terminator of the cauliflower mosaic virus (CaMV), described in the article of Franck et al. (1980) and the NOS terminator corresponding to the region in the non-coding 3' region of the nopaline synthase gene of the Ti-plasmid of the *Agrobacterium tumefaciens* nopaline strain (Depicker et al. 1992).

Preferably, the terminator used is the 3'CaMV.

According to the invention, the expression cassette, comprising a nucleic acid molecule having promoter activity specific to the pedicel as defined above, operatively linked to at least one nucleic sequence of interest may further comprise one or several selection marker genes for plants, useful for transformation and selection.

In the present invention, the term "selectable marker", "selectable gene", "selectable marker gene", "selection marker gene", "marker gene" are used interchangeably.

These selectable markers include, but are not limited to, antibiotic resistance genes, herbicide resistance genes or visible marker genes. Other phenotypic markers are known in the art and may be used in this invention.

A number of selective agents and resistance genes are known in the art. (See, for example, Hauptmann et al., 1988; Dekeyser et al., 1988; Eichholtz et al., 1987; and Meijer et al., 1991).

Notably the selectable marker used can be the bar gene conferring resistance to bialaphos (White et al., 1990), the sulfonamide herbicide Asulam resistance gene, sul (described in WO 98/49316) encoding a type I dihydropterate synthase (DHPS), the nptII gene conferring resistance to a group of antibiotics including kanamycin, G418, paromomycin and neomycin (Bevan et al., 1983), the hph gene conferring resistance to hygromycin (Gritz et al., 1983), the EPSPS gene conferring tolerance to glyphosate (U.S. Pat. No. 5,188, 642), the HPPD gene conferring resistance to isoxazoles (WO 96/38567), the gene encoding for the GUS enzyme, the green fluorescent protein (GFP), expression of which, confers a recognizable physical characteristic to transformed cells, the chloramphenicol transferase gene, expression of which, detoxifies chloramphenicol.

Advantageously, the selectable marker gene is inserted between a promoter and a terminator in a second expression cassette, said second expression cassette being integrated in the same vector as the expression cassette containing the nucleic sequence of interest under transcriptional control of a promoter according to the invention.

According to this advantageous embodiment, the marker gene is preferably controlled by a promoter which allows expression in cells, thus allowing selection of cells or tissue containing the marker at any stage of development of the plant. Preferred promoters are the promoter of nopaline synthase gene of *Agrobacterium*, the promoter derived from the gene which encodes the 35S subunit of cauliflower mosaic virus (CaMV) coat protein, and the rice actin promoter. However, any other suitable second promoter may be used.

Any terminator may be used. Preferred terminators are the 3'CaMV and Nos terminator as previously described.

Advantageously, the expression cassette containing the selectable marker gene is comprised between two Ds elements (transposons) in order for its removal at a later stage by interacting with the Ac transposase. This elimination system is described in Yoder et al. (1993).

For the transformation step, two vectors could be used, the first one comprising the expression cassette containing the gene of interest and the second one comprising the expression cassette containing the selectable marker gene. The same host cell being transformed with these two vectors (co-transformation).

The expression cassettes according to the invention may additionally contain transit peptide sequences. There are numerous examples in the art of transit peptides which may be used to deliver a target protein into a plastid organelle such as the small subunit (SSU) transit peptide of ribulose biphosphate carboxylase.

Other elements like introns and enhancers can also be present in the expression cassette of the invention in order to improve the expression of the nucleic sequence of interest.

Among useful introns, the first intron of maize adh1S can be placed between the promoter and the coding sequence. This intron when included in a gene construct increased the expression of the desired protein in maize cells (Callis et al., 1987). One also can use the $1^{st}$ intron of the shrunken 1 gene of the maize (Maas et al., 1991), the $1^{st}$ intron of the catalase gene of the bean catalase (CAT-1) (Ohta et al., 1990), the $2^{nd}$ intron of the ST-LS1 gene of potato (Vancanneyt et al. 1990), the DSV intron of the yellow dwarf virus of tobacco (Morris et al., 1992), the actin-1 intron (act-1) of rice (McElroy et al., 1990) and intron 1 of triosephosphate isomerase (TPI) (Snowdon et al., 1996). Preferentially, the intron used in the present invention is the Hsp70 intron or the Sh1 intron.

The expression cassettes may additionally contain 5' leader sequences. Such leader sequences can act to enhance translation. Such 5' leaders are known in the art and include, but are not limited to, picornavirus leaders, for example, the EMCV leader (Encephalomyocarditis 5' noncoding region) (Elroy-Stein, Fuerest, and Moss B., 1989); potyvirus leaders, for example, the TEV leader (Tobacco etch Virus) (Allison et al., 1986); the human immunoglobulin heavy-chain binding protein leader (BiP) (Macejack and Sarnow, 1991); the untranslated leader from the coat protein mRNA of alfalfa mosaic virus (AMV RNA 4) (Jobling and Gehrke, 1987); the tobacco mosaic virus leader (TMV) (Gallie et al., 1989); and the maize chlorotic mottle virus leader (MCMV) (Lommel et al., 1991). See also, Della-Cioppa et al. (1987). Other methods known to enhance translation can be utilized, for example introns, and the like.

Another object of the invention is any nucleotide vector referred to as an expression vector, such as a plasmid, which can be used for transforming host cells, characterized in that it contains at least an expression cassette as defined above. The construction of expression vectors for the transformation is within the capability of one skilled in the art following standard techniques.

The decision as to whether to use a vector, or which vector to use, is guided by the method of transformation selected, and by the host cell selected.

Where a naked nucleic acid introduction method is used, then the vector can be the minimal nucleic acid sequences necessary to confer the desired phenotype, without the need for additional sequences.

Possible vectors include the Ti plasmid vectors, shuttle vectors designed merely to maximally yield high numbers of copies, episomal vectors containing minimal sequences necessary for ultimate replication once transformation has occurred, transposon vectors, including the possibility of RNA forms of the gene sequences. The selection of vectors and methods to construct them are commonly known to persons of ordinary skill in the art and are described in general technical references (Mullis, K B (1987), *Methods in Enzymology*).

For other transformation methods requiring a vector, selection of an appropriate vector is relatively simple, as the constraints are minimal. The apparent minimal traits of the vector are that the desired nucleic acid sequence be introduced in a relatively intact state. Thus, any vector which produces a plant carrying the introduced DNA sequence should be sufficient. Also, any vector which introduces a substantially intact RNA which can ultimately be converted into a stably maintained DNA sequence should be acceptable.

However, any additional attached vector sequences which confer resistance to degradation of the nucleic acid fragment to be introduced, which assists in the process of genomic integration or provides a means to easily select for those cells or plants which are actually, in fact, transformed are advantageous and greatly decrease the difficulty of selecting useable transgenic plants.

The vector can exist, for example, in the form of a phage, a plasmid or a cosmid. The construction of such expression vectors for transformation is well known in the art and uses standard techniques. Mention may be made of the methods described by Sambrook et al. (1989).

Another object of the invention is a host cell, containing at least an expression cassette as described above.

The decision as to whether to use a host cell, or which host cell to use, is guided by the method of transformation.

The host cell can be any prokaryotic or eukaryotic cell. Any of a large number of available and well-known host cells may be used in the practice of this invention. The selection of a particular host is dependent upon a number of factors recognized by the art. These include, for example, compatibility with the chosen expression vector, bio-safety and costs. Useful hosts include bacteria such as *E. coli* sp. or *Agrobacterium*. A plant host cell, may be also used, notably an angiosperm plant cell, monocotyledon as dicotyledon plant cell, particularly a cereal or oily plant cell, selected in particular from the group consisting of maize, wheat, barley, rice, rape and sunflower, preferentially maize. The promoter according to the invention can also be used in cotton.

More particularly, the host cell used in carrying out the invention is *Agrobacterium tumefaciens*, according to the method described in the article of An et al., 1986, or *Agrobacterium rhizogenes*, according to the method described in the article of Jouanin et al., 1987.

The invention also concerns a transgenic plant or part of a transgenic plant, in particular fruit, seed, grain or pollen, comprising such a cell or generated from such a cell. Where the plant contains endogenously a SBT2 promoter according to the invention, it will be understood that the transgenic plant according to the invention comprises an additional "exogenous" SBT2 promoter, for instance integrated by transgenesis.

A whole plant can be regenerated from a single transformed plant cell. Thus, in a further aspect the present invention provides transgenic plants (or parts of them) including nucleic acid sequences in accordance with the invention. The regeneration can be performed by known methods.

The seeds which grow by fertilization from this plant also contain this transgene in their genome.

Advantageously, the transgenic plant obtained can produce grains with a larger endosperm in comparison with a non-transformed plant, particularly grains with starch, oil contents or protein contents which are modified in comparison with a non-transformed plant.

A plant or part of a plant according to the invention could be a plant or a part of it from various species, notably an angiosperm, monocotyledons as dicotyledons, preferably a cereal or oily plant, selected in particular from the group consisting of maize, rice, wheat, barley, rape and sunflower, preferentially maize. Said plant may also be cotton.

As used herein, the term "oily plant" denotes a plant that is capable of producing oil, and preferably that is cultivated for oil production. The hybrid plants in particular transgenic obtained by crossing plants according to the invention also form part of the invention.

Another object of the invention is a method of obtaining a plant having improved agronomic qualities and/or improved resistance to pathogens, comprising the steps consisting of:
  (a) transforming at least one plant cell by means of a at least a vector as defined previously;
  (b) cultivating the cell(s) thus transformed so as to generate a plant containing in its genome at least an expression cassette according to the invention, whereby said plant has improved agronomic qualities and/or improved resistance to pathogen.

According to the invention, "improved agronomic qualities" means improved agronomic qualities and/or improved nutritional qualities, notably yield, food or industrial qualities of a plant or a part thereof. Seed size, yield, seed number, seed composition are considered as elements conferring improved agronomic qualities to a plant as compared to a non-transformed plant (wild-type).

According to the invention, "improved resistance to pathogens" means that the transformed plant has a better resistance to pathogens than the non-transformed plant (wild-type).

The transformation of vegetable cells can be achieved by any one of the techniques known to one skilled in the art.

It is possible to cite in particular the methods of direct transfer of genes such as direct micro-injection into plant embryoids (Neuhaus et coll. 1997), vacuum infiltration (Bechtold at al. 1993) or electroporation (Chupeau et coll., 1989) or direct precipitation by means of PEG (Schocher et coll., 1986) or the bombardment by gun of particules covered with the plasmidic DNA of interest (Fromm Metal., 1990).

It is also possible to infect the plant with a bacterial strain, in particular *Agrobacterium*. According to one embodiment of the method of the invention, the vegetable cells are transformed by a vector according to the invention, the said cell host being able to infect the said vegetable cells by allowing the integration, in the genome of the latter, of the nucleotide sequences of interest initially contained in the above-mentioned vector genome. Advantageously, the above-mentioned cell host used is *Agrobacterium tumefaciens*, in particular according to the method described in the article by An et al., (1986), or *Agrobacterium rhizogene*, in particular according to the method described in the article by Guerche et al. (1987).

For example, the transformation of vegetable cells can be achieved by the transfer of the T region of the tumour-inducing extra-chromosome circular plasmid of *Agrobacterium tumefaciens*, using a binary system (Watson et al., 1994). To do this, two vectors are constructed. In one of these vectors the T region has been eliminated by deletion, with exception of the right and left borders, a marker gene being inserted between them to allow selection in the plant cells. The other partner of the binary system is an auxiliary plasmid Ti, a modified plasmid which no longer has any T region but still contains the virulence genes vir necessary to the transformation of the vegetable cell.

According to a preferred mode, it is possible to use the method described by Ishida et al. (1996) for the transformation of Monocotyledons.

According to another protocol, the transformation is achieved according to the method described by Finer et al., (1992) using the tungsten or gold particle gun.

Selection

The engineered plant material may be selected or screened for transformants (those that have incorporated or integrated the introduced nucleotide construction(s)). Such selection and screening methodologies are well known to those skilled in the art. The selection and screening method is chosen depending on the marker gene used.

An isolated transformant may then be regenerated into a plant.

Regeneration

Normally, regeneration is involved in obtaining a whole plant from the transformation process. The term "regeneration" as used herein, means growing a whole plant cell, a group of plant cells, a plant part or a plant piece (for example, from a protoplast, callus, or tissue part).

Methods of regenerating whole plants from plant cells are known in the art, and the method of obtaining transformed and regenerated plants is not critical to this invention.

In general, transformed plant cells are cultured in an appropriate medium, which may contain selective agents such as antibiotics, where selectable markers are used to facilitate identification, of transformed plant cells. Once callus forms, shoot formation can be encouraged by employing appropriate plant hormones in accordance with known methods and shoots transferred to rooting medium for regeneration of plants. The plants may then be used to establish repetitive generations, either from seeds or using vegetative propagation techniques.

The invention further relates to the use of at least an expression cassette as previously defined, for obtaining a transgenic plant exhibiting improved agronomic qualities and/or improved resistance to pathogen.

The agronomic quality of a plant is improved by acting in particular on the size of the embryo or of the endosperm and/or its development.

By way of example, the use of genes coding for hormones (cytokinins, auxins) under the control of the promoters described according to the invention, would make it possible to modify the process of cellularisation and thus the development of the endosperm.

An effect on the accumulation of nutrients can also be sought, by using for example, as nucleic sequences of interest, genes coding for transporters of nutrients (sugar in particular), or genes coding for inhibitors of these transporters, leading to differential accumulation of nutrients in the endosperm or embryo.

The invention also concerns the use of the transgenic plants obtained according to the invention, or parts of these plants, in particular seeds, grains, and fruits for preparing derived products, in particular food products.

The invention relates to seeds obtained from a plant transformed with a nucleic acid sequence according to the invention.

The products obtained, whether it be seeds with a higher oil content, flours of seeds or grains with a higher starch, protein or oil content, also come within the scope of the invention.

The invention also provides any composition for human or animal food prepared from the said obtained products.

The invention also relates to the Zm-SBT1 promoter (SEQ ID NO 3) that is specific to the aleurone, in particular in maize. Every embodiment described above may also be used with said promoter in place of the Zm-SBT2 promoter described above.

The present invention will be further understood in view of the annexed figures and following examples.

FIGURES

FIG. 1: Alignment of amino acid sequences deduced from a cDNA fragment encoding ZmSBT-1 (inside of a red box) to tomato P69 family Subtilisine proteinases. Red colour denotes amino acids equals in all proteins. The catalytically important Asp is indicated with asterisk inside of a black box and the arrow with the scissors indicate the N-termini of the mature enzymes in each protease. Alignment was made by AlignX using parameters assigned inVector NTI software. P69A—SEQ ID NO: 9; P69C—SEQ ID NO: 10; P69B—SEQ ID NO: 11; P69D—SEQ ID NO: 12; P69F—SEQ ID NO: 13; ZmSBT-1—SEQ ID NO: 14; P69E—SEQ ID NO: 15; Consensus—SEQ ID NO: 16

Figure 2:
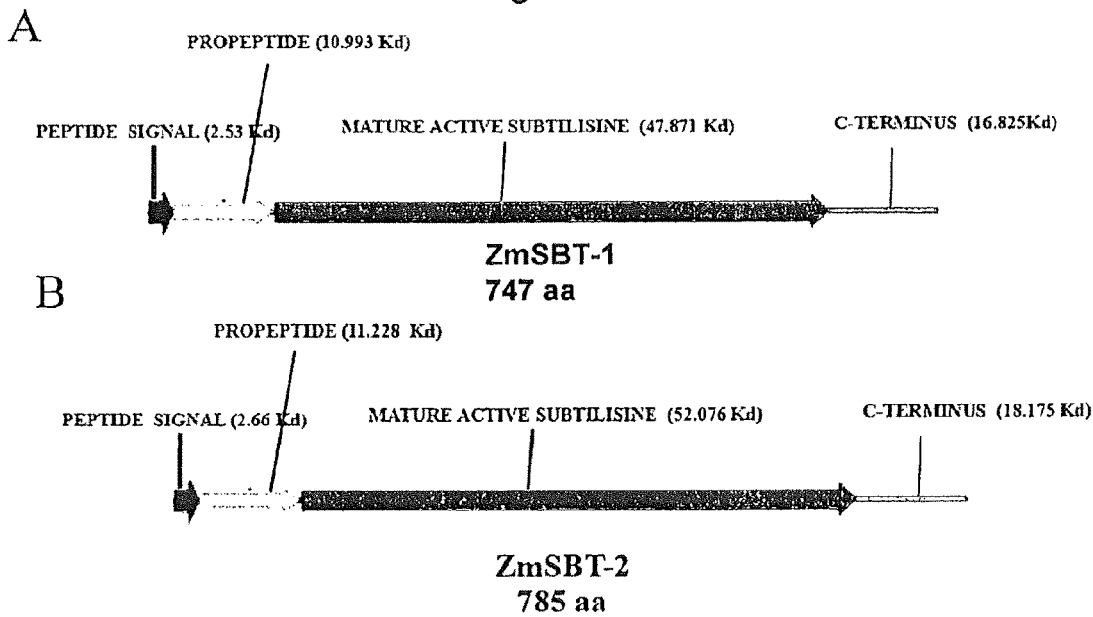

FIG. 2: Schematic diagram showing structural features and relative lengths of ZmSBT-1 (A) and ZmSBT-2 (B). Signal sequences are marked with purple arrows, prosequences are shown with green arrows, mature proteins are shown with red arrows and C-terminus are shown with grey lines.

Figure 3:
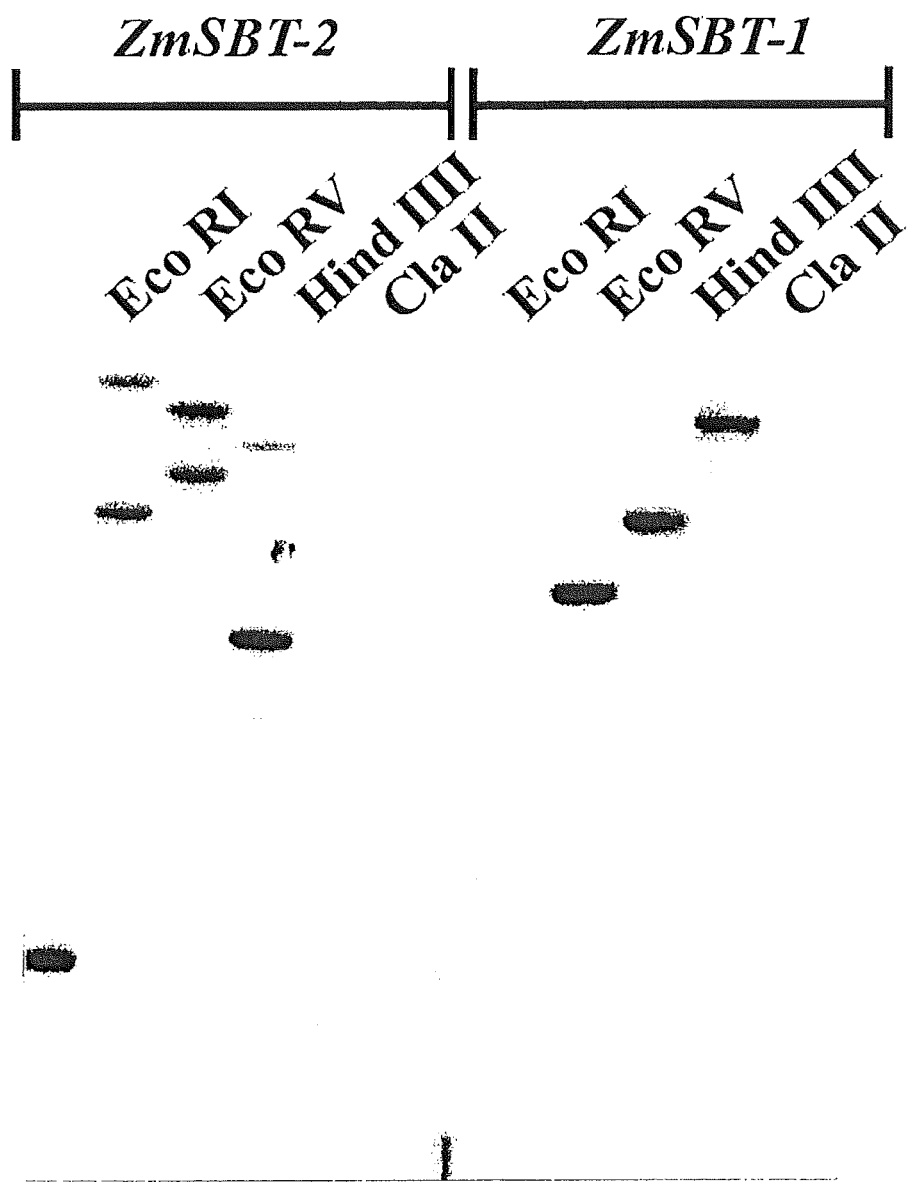

FIG. 3: ZmSBT-1 and ZmSBT-2Southern blot analyses. ZmSBT-1 is a single copy or low copy number gene and ZmSBT-2 is a double copy gene. Maize genomic DNA from the variety A69Y (15 µg per lane) was digested with Eco RI, Eco RV, Hind III and Cla I. The resulting Southern blots were hybridized with α-P32 ZmSBT-1 and ZmSBT-2 probes.

Figure 4:
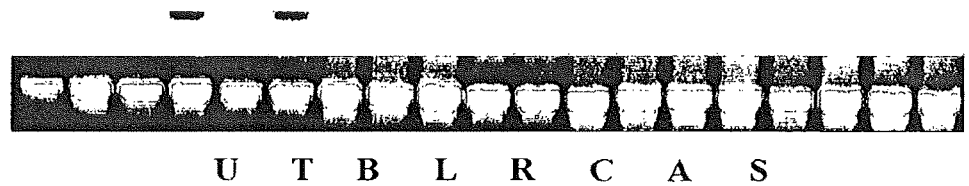
Figure 4:
Figure 4:
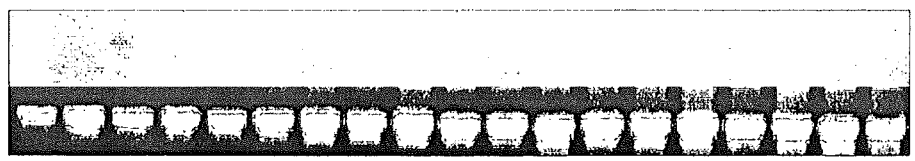
Figure 4:
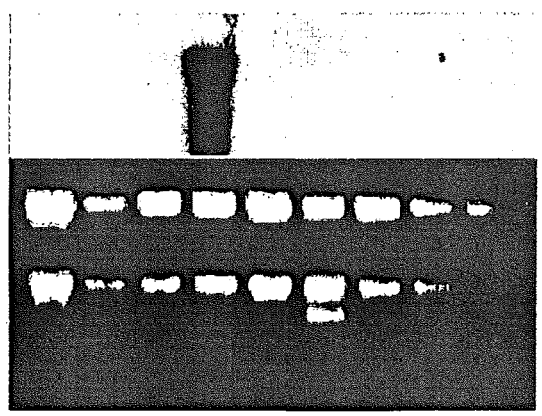

FIG. 4: Expression pattern of ZmSBT-1 (A) and ZmSBT-2 (B°) in different seed developmental stages and different maize tissues. (A) total RNA (20 µg per lane) from different seed developmental stage and different maize tissues were Northern blotted and hybridized with a ZmSBT-1 probe. U, unpollinated flowers; T, top half and B, bottom half from 8, 11, 14, 17, 20, 22, 24 and 32 dap seeds; L, leaves; R, roots; C, coleoptiles; A, anthers; S, silks. Images below show the ethidium bromide-strained geles before the transfer. (B) total RNA (20 µg per lane) from different seed developmental stage and total RNA (10 µg per line) from maize tissues were Northern blotted and hybridize with a ZmSBT-2 probe. T, top half and B, bottom half from 8, 11, 14, 17, 20, 22, 24 and 32 dap seeds; L, leaves; R, roots; C, coleoptiles; A, anthers; S, silks. Images below show the ethidium bromide-strained geles before the transfer. Numbers 3-32 refer to number of days after pollination (DAP). From 8dap, seeds were dissected before RNA extraction into upper (T) and lower (B) halves.

Figure 5:
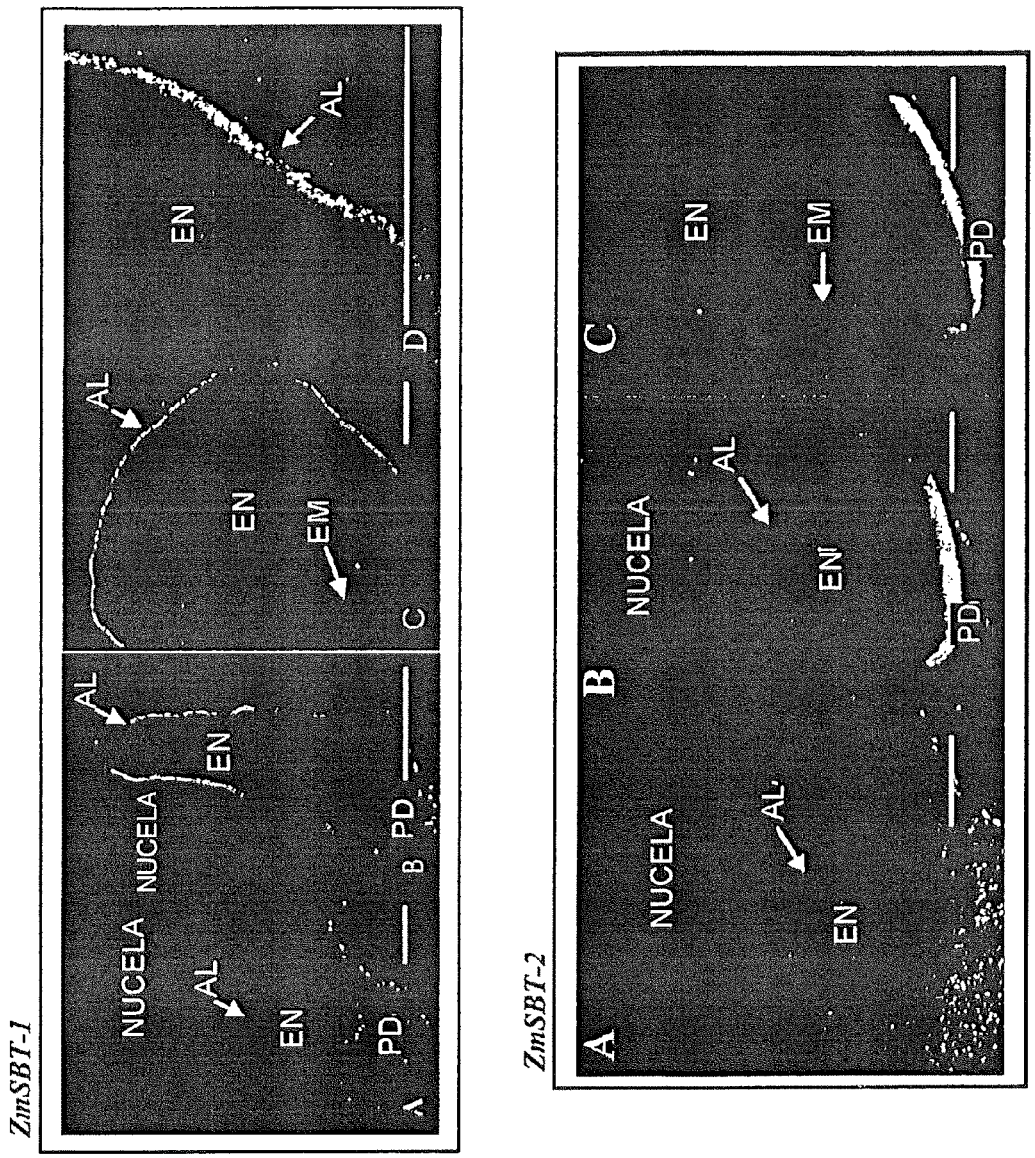

FIG. 5: In situ hybridisation of the ZmSBT-1 and ZmSBT-2 transcripts. ZmSBT-1: sagital sections of 6 dap (A, B) and 10 dap (C, D). Control sense probes produced no detectable signal (A°. Kernel were hybridised with antisense S35 labelled ZmSBT-1 probes. EN, endosperm; AL, Aleurone; PD, Pedicel. Bar=1 mm, A, B, C; 500 µm, D.

ZmSBT-2: sagital sections of 6 dap (A, B) and 10 dap (C, D). Control sense probes produced no detectable signal (A). Kernel were hybridised with antisense S35 labelled ZmSBT-2 probes. EN, endosperm; AL, Aleurone; PD, Pedicel. Bar=1 mm.

Figure 6:
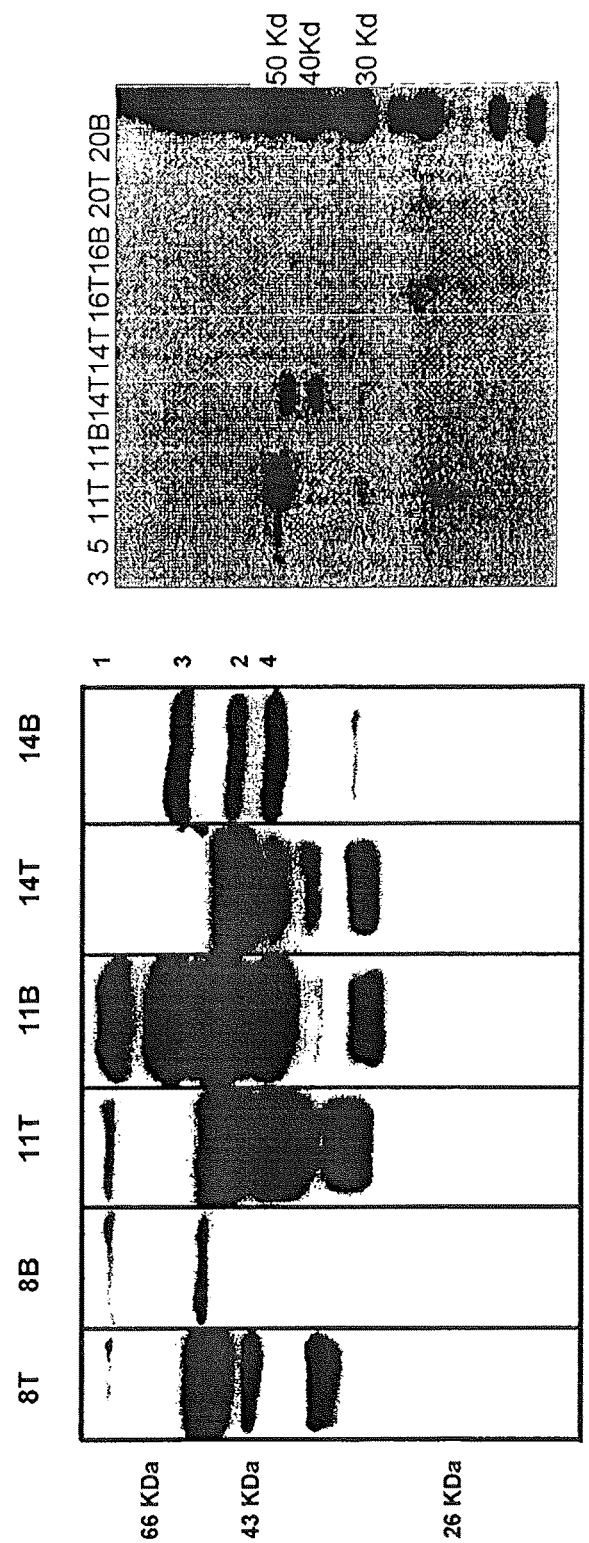

FIG. 6: Western blot analyses using the anti-ZmSBT-1 serum. Left panel: soluble proteins from immature kernel of different stages. Seeds (8, 11 and 14 dap) were dissected before protein extraction into their upper (T) and lower (B)

halves. Seed halves were reacted with the anti-ZmSBT-1 antibody (diluted 1:2000) and secondary antibody (diluted 1:20000). Right panel: total protein extracts from 3,5-dap whole kernel or 11, 14, 16 and 20-dap upper (T) or lower (B) seed halves were reacted with the anti-ZmSBT-1 antibody (diluted 1:2000) and secondary antibody (diluted 1:20000).

Figure 7:
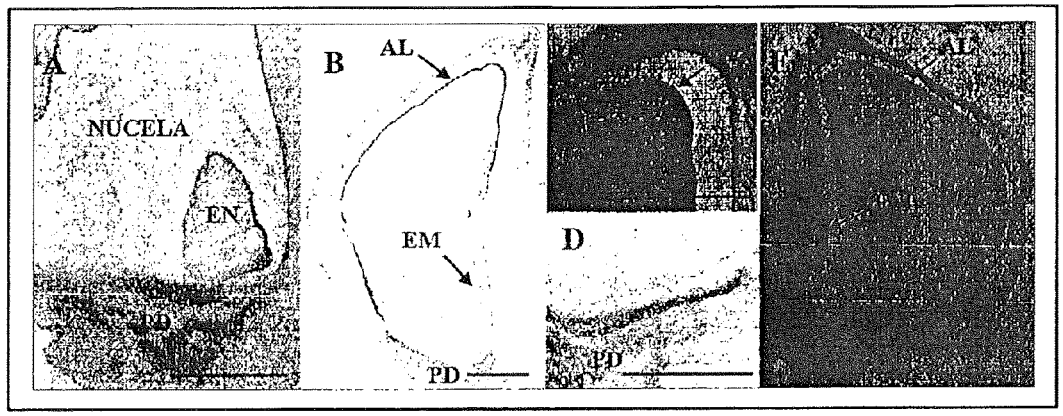
Figure 8:
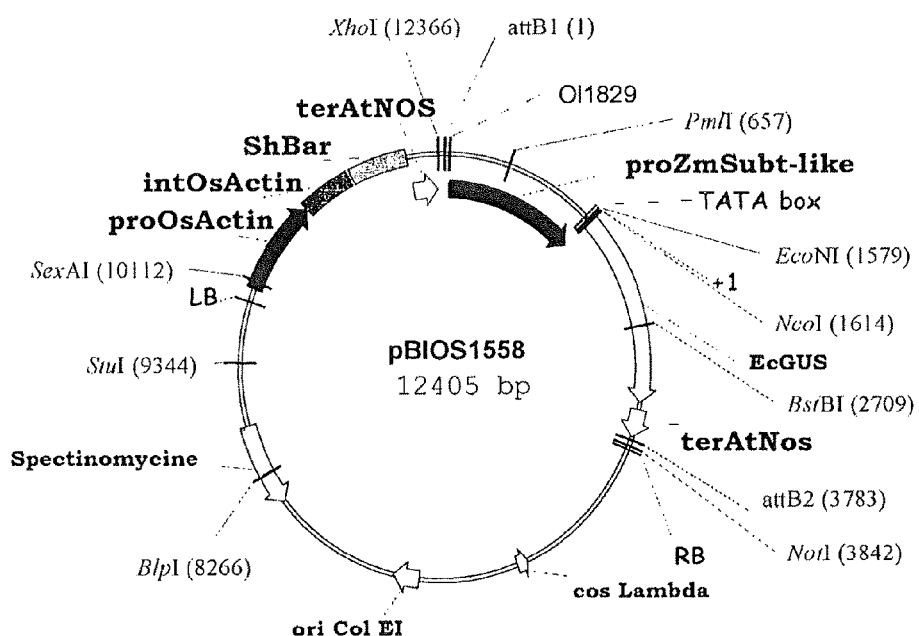

FIG. 7: Immunolocalisation of sagital sections of 3 DAP (A), 11 DAP (B, C, D) and 16 DAP (E). Kernels were reacted with the anti-ZmSBT-1 antiserum. Control experiments using pre-immune serum produced no detectable signal and are not shown. (C) and (D) are magnifications of (B). EN, endosperm; AL, Aleurone; PD, Pedicel; EM, embryo. Bars=1 mm. sections were staining with safranine stain FIG. 8: pBios 1558 vector.

Figure 9:
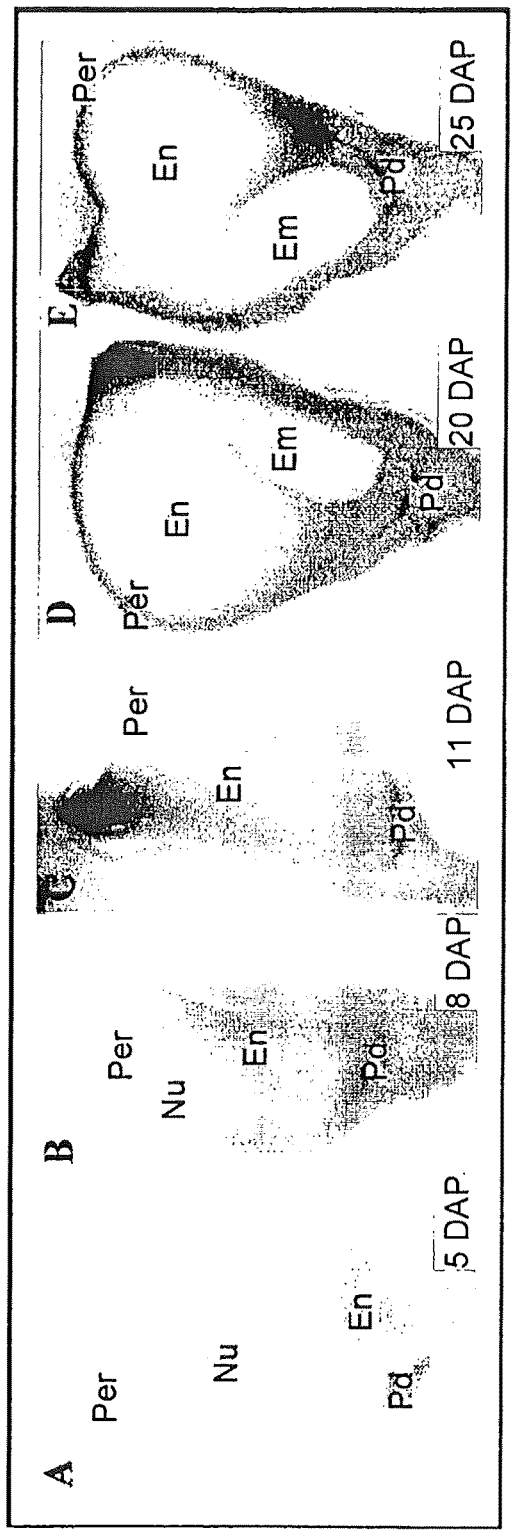

FIG. 9: GUS straining of immature maize seeds from promoter ZmSBT-1-GUS transgenic plants. Immature kernels at various stage of development were hand-dissected and strained as described in "Materials and Methods". En, endosperm; Pd, pedicel; Nu, nucela; Par, pericarpe; EM, embryon.

EXAMPLES

The invention will now be described by the way of the following examples, which should not be construed as in any way limiting the scope of the invention.

Several oligonucleotides and primers could be used to amplify or isolate the sequences or sequence fragments according to the present invention. The oligonucleotides and primers described are not limiting. The person skilled in the art knows how to design an oligonucleotide, or a specific oligonucleotide, based on a sequence.

Material and Methods:
Plant Material

Maize plants (Zea mays, line A69Y) were grown in a greenhouse under a 16 h light, 8 h dark photoperiod, with supplemented illumination and a temperature of 20-25° C.

Arabidopsis plants (Arabidopsis thaliana, line Columbia) were grown in short days (12 h light and 12 h dark cycle) to get large plants and greater seed yield for three weeks and later these plants were grown in long days (16 h light and 8 h dark cycle) to induce bolting.

Differential Screening

The lambda 10 DAP kernel library was described by Hueros et al (1995). RNA obtained from 8 DAP seeds, 21 DAP seeds, and the top or bottom half of 10 DAP seeds was used to synthesize subtracted probes employing the PCR Select kit (Clontech, Mountain View, Calif., USA). Six thousand clones from the library were randomly selected and their inserts PCR amplified with universal/reverse pBluescript primers. The products were electrophoresed on 1.5% agarosa gels and transferred to charged nylon membranes (Roche Applied Science, Penzberg, Germany). These filters were hybridized with $^{32}$P labelled probes obtained by random priming (rediprime II Labelling kit, Amershan, UK) of 8 DAP, 21 DAP, top half 10 DAP and bottom half 10 DAP subtracted cDNA samples, and a mixed roots plus leaves unsubtracted cDNA samples. This identified transcripts with preferential expression in defined tissue/time frame. The hybridization signal of each clone with each probe was recorder in a range from no signal (−) to very strong signal (++++).

Preparation of Full Length cDNA

To obtain the 5' terminus of cDNA, the Marathon$^{TH}$ cDNA Amplification kit (Clontech) was used, following the manufacturer's instruction. Once obtained, new primers were designer and the full length cDNA was amplified from 10 DAP seed mRNA.

Southern and Northern Blots

DNA (15 μg) was digested with EcoRI, EcoRV, HindIII and ClaI endonucleases, electrophoresed and transferred to charged nylon membranes (Roche). Total RNA (20 μg) from each of the following samples (unpollinated flowers, leaves, roots, coleoptiles, silks, anthers, whole seeds at 3, 5, 6 DAP and the top and bottom halves of 8, 11, 14, 16, 20, 22, 24 and 32 DAP seeds) were electrophoresed in 1.5% under denaturing conditions (6% formaldehyde) and transferred to charged nylon membranes (Roche).

Blotting procedures were as described by Hueros et al. (1995). Probes were made by means of PCR amplified with universal/reverse pBluescript or internal sequence primers of cDNA clones. These amplifications products were labelled with $^{32}$P for Southern and Northern blots. Hybridization, washing of the membranes, and auto radiographic detection for each technique were performed as described by Hueros et al. (1995).

In Vitro Protein Synthesis and Antibody Production

The coding sequence of ZmSBT-1 (without coding sequence of the signal peptide) was cloned between the Ava I and Sma I sites of the pIVEX 2.4a vector (which adds 6 histidine tail to the N-terminal end of the protein) by means of two primers with a site Ava I and Sma I in each one, respectively. This was used to produce the peptide in an HY 500 in vitro transcription/translation system, based on an E. coli extract (Roche). Protein solubility and integrity was tested by Western blotting, using a primary mouse anti His antibody (Qiagen GmBH, Hilden, Germany) to detect the His tagged protein, and a secondary anti-mouse antibody conjugated to horseradish peroxidase (Sigma-Aldrich, St. Louis, Mo., USA). Detection was based on the Super Signal West Pico Chemiluminescent Substrate (Pierce Biotechnology, Rockford, Ill., USA). The resulting protein was solubilized in 8M urea, affinity purified using Ni-NTA agarosa (Qiagen), and dialysed against 1M urea 0.5% SDS. The protein yield of the procedure was quantified using the Bradford reagent (Bradford et al. 1976). Four 100 μg doses were injected into rabbits over 56 days in order to obtain a polyclonal serum.

Western Blot Experiments

For protein extraction the top and bottom halves of 8, 11 and 14 DAP maize seeds were grinded in liquid nitrogen with a pestle and a mortar. The powder was then extracted with 0.05M sodium phosphate buffer pH 7 containing 2 mM pefabloc (Roche), 0.1% β-mercaptoethanol and 1 mM EDTA, under agitation and at 4° C. Cell debris were removed by centrifugation at 12000 rpm for 10 min at 4° C. The supernatant was mixed with ½ volume of protein loading buffer (Laemmli, 1970). Protein samples (30 μg per lane) were fractionated in 15% denaturing SDS-PAGE gels under standard methods and electroblotted onto Inmobilon P membranes (Millipore, Bedford, Mass., USA). The membrane was treated with a 1:2000 dilution of anti-ZmSBT-1 and detected with rabbit-radish peroxidase coupled second antibody (Sigma, USA) at a 1:20000 dilution and with the Supersignal West Pico Chemiluminescent substrate (Pierce, USA).

In a second case, the 3 and 5 DAP kernel and the top and bottom halves of 11, 14, 16 and 20 DAP maize seeds were grinded in liquid nitrogen. The powder was extracted with protein loading buffer (Laemmli, 1970) containing 1 mM EDTA, 1 mM phenymethylsulphonylfluoride. These proteins (30-50 μg per lane) were then separated on 12% pre-cast NuPAGE Novex gels (Invitrogen, Carlsbad, Calif., USA) using a 3-(N-morpholine)-propanesulphonic acid (MOPS)

buffer system. Transference to a polyvinylidene fluoride filter (Millipore, Bedford, Mass., USA) was also performed using the Invitrogen apparatus and buffers. The filter was then subjected to immunodetection with the ZmSBT-1 antiserum at a 1:2000 dilution and detected with rabbit-radish peroxidase coupled second antibody (Sigma, USA) diluted 1:40000. The signal was detected using a chemiluminescent substrate (Super Signal West Pico Chemiluminescent substrate. Pierce, USA).

In Situ Hybridisation, Immunolocalization

Maize seeds were collected at different DAP and fixed in 4% paraformaldehyde, 0.1% glutaraldehyde and 0.1M sodium phosphate buffer pH 7.2 for 12-24 h depending on the tissue volume at 4° C. Samples were dehydrated and embedded in wax (Paraplast, Sigma, USA) using xylol as solvent. Sections 8 μm thick were affixed to glass slides treated with 3-aminopropyltriethoxylane. Sections were deparaffinised in xylol and rehydrated through an ethanol series. For the in situ hybridisation, 35S labelled antisense and sense probes were synthesised using T3 and T7 polymerases (Boehringher-Manheim, Germany) from linearised pBluescript SK+ plasmid containing a fragment of ZmSBT-1 or ZmSBT-2 genes. Probes were partially hydrolysed with sodium carbonate. Sections were hybridised as previously described (Hueros et al. 1995), following the method of Cox and Goldberg (1988).

For the immunolocalisation experiments, inhibition of endogenous peroxidase was carried out by incubating the sections in 0.3% v/v $H_2O_2$ in methanol for 30 minutes. Tissue was then washed in PBS and blocked with 2% normal donkey serum (Chemicon International, USA) in PBT/BSA for 20 minutes at room temperature. Sections were incubated with anti-ZmSBT-1 serum or pre-immune serum diluted 1:400 in PBT/BSA for 1 h at room temperature. Tissue was then washed in PBT and sections were incubated with anti-rabbit IgG biotin conjugate (Sigma, USA) diluted 1:800 for 30 minutes at room temperature. Sections were washed in PBT again and later tissue was incubated with anti-biotin avidin-proxidase conjugate (Sigma, USA) diluted 1:100 for 30 minutes at room temperature. The immunoreaction was detected using 3,3'-diaminobenzidine tetrahydrochloride with metal enhancer tablet sets (Sigma, USA) as substrate.

Construction of Plasmids for Obtain Maize and Arabidopsis Transgenic Plants

A BAC clone containing ZmSBT-1 gene was obtained. A fragment of 7000 bp from this BAC (containing ZmSBT-1 coding sequence, 1000 bp downstream and 3500 bp upstream) was isolated and ligated into the Eco RV site of pBluescript and sequenced. This 3500 bp localised upstream of the coding region was amplified by a PCR with primers (SEQ ID NO 4 SBT-B1: 5'-GGGGACAAGTTTGTA-CAAAAAAGCAGGCTTATCGATGAGCCTGAAG-3' and SEQ ID NO 5 SBT-B2: 5'-GGGGACCACTTTGTACAA-GAAAGCTGGGTATGGCAGAGACTTGGAAGATG3'). The product of this amplification was used to several recombination assays in order to introduce the promoter sequence in different entry vectors: pDONR 221 (Invitrogen, USA) and pDONR AMP. The first construction was used to introduce ZmSBT-1 promoter sequence in pBIOS 969 (Binary vector BIOGEMMA copyright with GUS informer gene) and to obtain maize transgenic plants. The second construction was used to introduce ZmSBT-1 promoter sequence in pDEST-pBI101.3 (pDEST-pBI101.3 plasmid, Clontech, Jefferson et al. 1986, containing GUS reporter gene) and to obtain Arabidopsis transgenic plants.

Transformation of Arabidopsis

Transformation of Arabidopsis thaliana was mediated by Agrobacterium tumefaciens C58C1::pM90 following the method of Clouth and Bent (1998).

Example 1

Identification of an Endosperm Specific Subtilisin-Like Protease Gene

In order to identify genes differentially expressed during maize kernel development, an expression database was built from 6000 transcripts randomly selected from a 10 days after pollination (DAP) endosperm cDNA library, using a differential screening method. Clones 14-15A and 24-27 showed moderate hybridization to a subtracted probe specific for the top half of the kernel, but no signal with any other probe in the set. These clones carry overlapping region of the same gene (850 by and 650 by long insert respectively) encoding a protein with significant similarity to a serine protease of the subtilisin family. A third clone, 26-42 (1000 by long insert), that showed no signal with any probe, corresponded to another overlapping region of this subtilisin-like protease gene. Overlapping clone sequence was compared with public database and it was truncated in 1200 by with regard to a full length cDNA. RACE experiments were performed to obtain the 5'end of this subtilisin-like protease transcript. The putative full length cDNA was 2330 by long, encoding a 747 amino acid protein with a predicted molecular weight of 78.245 KDa. As shown in FIG. 1, this protein is similar to others Subtilisin-like proteases described in plants (P68A, CAA76724; P69B, CAA76725; P69C, CAA76726; P69D, CAA76727; P69F, CAA06414, P69E, CAA06413). The typical catalytic triad as well as catalytically important Asn, which is responsible for the stabilization of the transition state oxyanion, can be found in the deduced amino acid sequence of this Subtilisin-like protease cDNA. The gene was therefore named ZmSBT-1 (Zea mays Subtilisin-1).

ZmSBT-1 encodes a preproprotein (FIG. 2). At the N-terminus, a stretch of hydrophobic amino acids is found which is typically encountered in signal peptides (24 amino acids, 2.53 kDa) responsible for targeting the protein to the secretory system. The signal peptide is followed by a propeptide (96 amino acids, 10.993 kDa) which may aid in folding of the protein and/or act as an intramolecular inhibitor of enzymatic activity (Siezen et. al. 1995; Ujwal and Masayori 1996). Finally, removal of the C-terminus of ZmSBT 1 (152 amino acids, 16.825 kDa) produces an active mature protein (474 amino acids, 47.871 kDa).

ZmSBT-1 is a Single-Copy Gene in Maize

The insert in clone 24-27 was $^{32}$P-labelled and used to determine the copy number by hybridization to genomic DNA digested with different restriction endonucleases. The probe hybridized to a single DNA fragment in all cases, indicating that ZmSBT-1 is a single copy gene in maize (FIG. 3). Primers designed to amplify the coding sequence of ZmSBT-1 were also used to amplify its genomic sequence from maize genomic DNA. This PCR product demonstrated that ZmSBT-1 was intronless.

From one library of BAC clones, a C5 BAC clone contained ZmSBT-1 sequence was obtained. This clone was used to isolate the 3500 by sequence located immediately upstream of the translation start site of ZmSBT-1. This ZmSBT-1 promoter fragment was fused to GUS and used to transform maize and Arabidopsis plants mediated by Agrobacterium tumefaciens.

ZmSBT-1 is Expressed Exclusively in the Endosperm of the Maize Kernel within a Short Developmental Time Frame The expression pattern of ZmSBT-1 in different maize tissues and at several developmental stages of the seed was studied by Northern blot analyses (FIG. 4). The transcript was detected only in immature kernels, being undetectable in the other samples of vegetative or reproductive tissues analysed. Within the seed, expression was first detected at 5 DAP, transcript accumulation reaches a maximum around 11 DAP and declines afterwards, being undetectable around 14 DAP. RNAs from upper and lower halves of the kernels were separately analysed in the Northern blot shown in FIG. 4 for kernels older than 8 DAP (T means upper and B means lower), the results show that the transcript is found in both parts, but it is principally accumulated in the top part of the seed.

ZmSBT-1 is Expressed Exclusively in the Aleurone Layer

In order to determine the precise localisation of the ZmSBT-1 transcripts, a S-labelled antisense RNA probe was produced and used for in situ hybridization experiment with longitudinal sections of maize kernels at different stages of development (FIG. 5). The aleurone cell layer was the only kernel tissue to show positive hybridization signals with the antisense probe. In agreement with the results obtained in the Northern analyses, the signal was detected already 6 DAP and reached a maximum at around 10 DAP. It was not detectable to 16 DAP (not shown). No signal was detected with a sense probe used as a negative control (not shown).

Localisation of the ZmSBT-1 Protein

Western blot analyses using ZmSBT-1 antiserum showed high specificity reaction with proteins from the maize corn extracted in absence of detergents. The anti-ZmSBT-1 antibody detected several bands, which can be analyzed on the basis of two factors: ZmSBT-1 protein undergoes a translational process that will yield different intermediates peptides. These intermediates peptides can be detected in Western blot analyses, so the band number 1 (75.7 kDa) would have an equivalent molecular weight similar to the one predicted for ZmSBT-1 in propeptide form and the band number 2 would have an equivalent molecular weight similar to the one predicted for ZmSBT-1 in mature form (47.9 kDa). The second factor is that anti-ZmSBT-1 antibody is recognizing a second Subtilisin from maize kernel, which is specifically accumulated in the lower halves of the kernels. The pattern of accumulation of this second protein, bands numbers 3 and 4 (FIG. 6, left panel), is different from ZmSBT-1 protein, which is located in proteins extracts from both upper and lower halves of the kernels. Western blot analysis using different conditions of detection, mainly diluting antibody concentration, showed the anti-ZmSBT-1 antiserum detected the band number 2 only in protein extracts from upper half of the kernel with the expected size for ZmSBT-1 in mature form (47.9 KDa). The signal from ZmSBT-1 and the second Subtilisin located in bottom part disappeared (FIG. 6, right panel).

In agreement with the results obtained in the in situ hybridization, immunolocalization experiments showed that the ZmSBT-1 protein accumulates in the outer endosperm cells, in the aleurone layer. The signal intensity in the aleurone layer reached a maximum at around 11 DAP (FIG. 7). Although ZmSBT-1 transcript was not detectable at 16 DAP the ZmSBT-1 protein was still detectable in this stage, but intensity of the signal had decreased. Interestingly, a second signal was detected in bottom part of the kernel too, in the placentochalaza. Nevertheless the location and accumulation dynamics of this second protein indicates that ZmSBT-1 antiserum is recognizing a second protein related to ZmSBT-1.

Example 2

ZmSBT-2, a Second Subtilisin-Like Protease Gene Exclusively Expressed in Maize Kernel In order to identify this second gene expressed in plazentochalaza region, a search in our expression database was carried out. A cDNA clone encoding a protein related to ZmSBT-1 was found. This cDNA showed moderate hybridization to a subtracted probe specific for the bottom half of the kernel, but no signal with any other probe in the set. The putative 2500 by full length cDNA was obtained by means of ESTs public databases. The encoded protein has a predicted molecular weight of 84 KDa and a total of 785 amino acids. The gene was therefore named ZmSBT-2 (*Zea mays* Subtilisin-2). The computer based comparison of amino acid sequence of the $NH_2$ terminus indicated the existence of a pre-pro-sequence, consisting of a hydrophobic signal peptide at the extreme $NH_2$ terminus (24 amino acids, 2.66 kDa.), followed by a 101 amino acid pro-sequence (11.228 kDa) which is a typical feature of proteases of Subtilisin proteases. The proteolytic removal of the pro-sequence is an important step in the generation of the active protease from the inactive zymogen (Zhou et al. 1995). Removal of the C-terminus of ZmSBR2 (107 amino acids, 18.174 kDa) produces an active mature protein (553 amino acids, 52.076 kDa).

Genomic DNA gel blot analysis in the inbred line A69Y demonstrated that, unlike ZmSBT-1 gene, ZmSBT-2 has two copies gene in maize (FIG. 3). These results demonstrate the fact that cross hybridization does not exist among ZmSBT-1 and ZmSBT-2.

Expression analysis by means of Northern blot confirmed ZmSBT-2 gene is expressed exclusively in the basal kernel (FIG. 4). The ZmSBT-2 transcript was detected in un-pollinated female flowers, indicating this gene is expressed before the double fertilization happens. In situ hybridization analysis showed ZmSBT-2 transcript is specifically accumulated in plazentochalaza cells (FIG. 5). These results support the fact that anti-ZmSBT-1 antibody recognizes both ZmSBT-1 and ZmSBT-2 proteins. It is likely that specific bands detected in proteins extracts from lower halves of the seed in Western blot experiments come from peptides of ZmSBT-2 protein, but since a specific ZmSBT-2 antibody was not produced, it was impossible to specify exactly each one.

Example 3

A 3552 bp Promoter Sequence from ZmSBT-1 Directs the Expression of the Gus Reporter Gene in the Endosperm Aleurone Cell Layer The ability of this promoter fragment to confer aleurone cell specific expression in transgenic maize was tested by maize transformation with the GUS reporter gene. Three independent transgenic lines (EUG 4A, EUG 10A y EUG 14A) were obtained and analyzed in detail. Plants containing the GUS gene were identified by PCR analysis. The transgenic lines were further analyzed by Southern blot using Sac I, an enzyme that does not cleave within the reporter gene. Probing Sac I digested DNA with the GUS coding sequence gave different patterns of hybridization for each transgenic line (a single copy and three copies integration in EUG 4A and EUG 10A, respectively), confirming their independent origin.

Histochemical staining of leaves, roots and adventitious roots for GUS did not give signals for any transgenic line analyzed (not shown). The transgenic plants were self-pollinated and the developing kernels were stained for GUS enzyme activity at various stages during development. Results showed in FIG. 9 demonstrate that a 3552 bp promoter sequence from ZmSBT-1 represented by SEQ ID NO 3 is capable of directing specifically the expression of the GUS reporter gene in the endosperm aleurone cell layer from early stages (5 DAP), reaching a maximum around 11 DAP and declining afterwards. At later stages of seed development (20-25 DAP), when Northern blot and in situ hybridizations analyses showed ZmSBT-1 is not expressed, the GUS signal remained confined to the upper aleurone cells, which can be explained for a very stable GUS protein in the plant cell.

Promoter Sequence from ZmSBT-1 Directs the Expression of the Gus Reporter Gene in Developing Tissues of *Arabidopsis thaliana*

To investigate in detail the spatial pattern of expression of ZmSBT-1 gene in *Arabidopsis thaliana*, promoter region (SEQ ID NO 3) was fused to the β-glucuronidase (GUS) reporter gene in plasmid pBI101.1 to generate construction pDEST.pBI101.3 PROMSBT-GUS (pZmSBT-1::GUS). This construction was introduced into *Arabidopsis* plants by transformation with *A. tumefaciens* and forty two independent kanamycin resistant transformants were generated. Expression of GUS activity driven by ZmSBT-1 promoter was detected in several developing tissues: roots meristems, shoots meristems, inflorescences (in stigmas), siliques, seeds and expanding leaves (not shown). This expression was transitory because it disappeared once the tissues had matured. GUS signal was detected in the whole surface of younger leaves, with a peak in the nerves and in the base of the trichomes. Afterwards, the intensity of the signal remained restricted to the nerves of leaves and not GUS signal was detected in mature leaves. In siliques, GUS signal was detected in pods and seeds, but the intensity of the signal was decreasing significantly as the time was spent. Also, GUS activity could be observed at sites where new lateral roots were emerging. These results support ZmSBT-1 gene is expressed in developing tissues.

ZmSBT-1 Gene Expression Depend on Aleurone Cell Fate

To determinate whether the ZmSBT-1 is involved in the same regulatory pathway than DEK1 and CR4, we examined both ZmSBT-1 transcript and ZmSBT-1 protein expression in dek1 and cr4 mutants. This analysis revealed that ZmSBT-1 transcript is absent in 7 and 15 DAP dek1 mutants seeds, in which no aleurone layer develops and the peripheral cell layer of this endosperm shows characteristics of starchy endosperm (Becraft and Asuncion Crabb, 2000; Lid et al., 2002). In order to confirm the absence of a correctly aleurone layer developed, in situ hybridization with a second aleurone cell marker, BETL9 Like, was carried out. BETL9-Like gene is specifically expressed in aleurone cell layer from the first days of the development up to 25-30 DAP.

Dek1 mutant kernels hybridised with this second probe showed no BETL9 Like expression too. In situ hybridization in wild type siblings showed a normal expression of both ZmSBT-1 and BETL9 Like markers, even so at 15 DAP when BETL9-Like is expressed but not ZmSBT-1 transcript. Immunolocalisation assays in dek1 mutants supported the in situ results. ZmSBT-1 protein was absented in 7 and 15 DAP dek1 mutant kernels too.

On the other hand, in situ hybridization with cr4 mutant seeds revealed that ZmSBT-1 transcript is expressed in several outer layer of endosperm both at 5 DAP and at 14 DAP. These results were confirmed with BETL9 Like probe, which was detected in several outer layer of cr4 mutant kernels too and only in the most external layer of endosperm in wild type siblings. The same expression pattern was also observed in immunolocalisation assays at 5 DAP, 11 DAP and 14 DAP with anti-ZmSBT-1 antibody. Sections of cr4 mutant kernels showed patches of several peripheral layers accumulating ZmSBT-1 protein, which could be explained by a wider spatial distribution of the signal, normally triggering outer.

Example 4

A 1556 bp Promoter Sequence from ZmSBT-2 Directs the Expression of the Gus Reporter Gene in the Pedicel The *Zea mays* SBT-2 promoter (SEQ ID NO 1) fragment have been amplified from *Zea mays* inbred line B73. A 961 bp fragment of the sequence was amplified by primers OI1813 (SEQ ID NO 6-reverse: CCATGGTGGCTGCTGTTG-GATG-TGTGTGTGAGCTC) and OI1814 (SEQ ID NO X-forward: GATTGGCACG-TGTTTCAAGTGC) and cloned into pGEM-T easy leading to pBIOS 1541. The 3' fragment of the promoter was amplified by primer OI1829 (SEQ ID NO 7-reverse: GGTACCAAGAGTTTCGTAGTC-CTGGAG) and primer OI1815 (SEQ ID NO 8-forward: GCATGCATTTGGGCATGTCCC). This −1536 to −870 fragment was cloned into pGEM-T easy leading to pBIOS 1542.

pBIOS 1543, was constructed by introduction of the PmII/PstI fragment (proZmSubt-like_961 bp) from pBIOS1541 into pBIOS1542 (proZmSubt-like (−1536 to −870) opened with PmII/PstI.

pBIOS 1554 was constructed by introduction of Zm-SBT2 promoter for driving expression of GUS.

pBIOS 1558 (FIG. 8) was obtained by introduction of said Zm-SBT2/GUS expression cassette in a *Agrobacterium* adapted vector.

The plasmid pBIOS 1558, was then introduced in pSB 001 by homologous recombination in *A. tumefaciens*, leading to pRec 1558, according to Komari et al. (1996) and the Maize cultivar A188 was transformed with this agrobacterial strain as described by Ishida et al. (1996).

The expression of the SBT2 promoter Gus reporter gene is observed on T2 seeds at 7 d.a.p. (day after pollination), on 15 dap and on the mature seeds to confirm the specific expression of this promoter.

Example 5

A 1557 bp Promoter Sequence from ZmSBT-2 Directs the Expression of the Gus Reporter Gene in the Pedicel Maize plants were transformed by an expression cassette comprising SEQ ID NO 2, driving expression of the GUS protein, as described in example 4.

REFERENCES

An et al. (1986), Plant Physiology, 81:86-91
Allison et al. (1986); the MDMV leader (Maize Dwarf Mozaic Virus), Virology, 154:9-20
Andersen M N et al., (2002), Plant Physiol. October; 130(2): 591-604.
Balandín, M. et al., (2005). Plant Molecular Biology. Vol 58: pp 269-282.

Bechtold (1993), Comptes rendus de l'academie des sciences, 316(10) p 1194-1199.
Becraft, P. W. y Asuncion-Crabb, Y. (2000). Development 127, pp. 4039-4048.
Becraft, P. W. (2001). Cell & Developmental Biology, vol. 12, 2001: pp. 387-394.
Becraft, P. W., et al., (2001). Plant Physiology, October, Vol. 127, pp. 486-496.
Bevan et al. (1983), Nature, 304:184-187
Berger, D. y Altmann, T. (2000). Genes & Development. Vol. 14: pp 1119-1131.
Bradford, M. M. (1976). Analytical Biochemistry. Vol. 7, pp. 248-54.
Bolchi, A., et al., (1999) Plant Mol. Biol. 39 (3), 527-537.
Callis et al. (1987), Genes Dev., 1:1183
Chupeau, M C et al 1989. Biotechnology vol. 7: pp. 503-508
Clough, S. L. y Bent, A. F. (1998). Plant Journal. Vol. 16, pp. 735-743.
Cox, K. H. and Goldberg, R. B. (1988). Plant Molecular Biology: A Practical Approach, IRL Press, Oxford, pp. 1-35.
Dekeyser et al. (1988), Plant Physiology, 90:217-223
Della-Cioppa et al. (1987), Plant Physiology, 84:965-968
Depicker et al. (1992), Mol. Gen. Genet., 235(2-3):389-396
Eichholtz et al. (1987), Somatic Cell and Molecular Genetics, 13:67-76
Elroy-Stein, O., Fuerest, T. R., and Moss B. (1989), PNAS USA, 86:6126-6130
Finer J. (1992) Plant Cell Report 11: 323-328.
Franck et al. (1980), Cell, 21(1):285-94
Fromm M E, et al., (1990), Biotechnology (NY). September; 8(9):833-9.
Gallie, D. R. et al. (1989), Molecular Biology of RNA, pages 237-256
Gritz et al. (1983), Gene, 25:179-188
Guerche et al. (1987), Mol. Gen. Genet., 206:382
Hauptmann et al. (1988), Plant Physiology, 86:602-606
Hueros, G., et al., (1995). Plant Cell 7, 747-757.
Ishida et al., (1996), Nature biotechnology, 14, 745-750
Jang et al., (1997) Plant Cell, 9, 5-19
Jefferson, R. A., et al., (1986). Proceedings of the National Academy of Sciences USA. Vol. 83, pp. 8447-8451.
Jobling, S. A., and Gehrke, L. (1987), Nature, 325:622-625
Jouanin et al. (1987), Plant Science, 53:53-63
Jordá, L., et al., (1999). The journal of biological chemistry. Vol. 274, No. 4, Issue of January 22, pp. 2360-2365.
Jordá, L., et al., (2000). Plant Physiology. January. Vol. 122, pp. 67-73.
Jordá, L. y Vera, P. (2000). Plant Physiology. November. Vol. 124, pp. 1049-1057.
Kaneda, M. y Tominago, N. (1975). Biochemistry. Vol. 78, pp. 1287-1296.
Komari et al., (1996), Plant Journal, 10(1) 165-174
Laemmli, U. K. (1970). Nature. Vol. 277, pp. 680.
Lid, S. E., et al., (2002). PNAS. April, 16. Vol 99, No 8, pp 5460-5465.
Lobreaux S. et al., (1992). Plant Molecular Biology 19: 563-575.
Lommel, S. A. et al. (1991), Virology, 81:382-385
Maas et al. (1991), Plant Molecular Biology, 16:199
Macejack, D. G., and P. Sarnow (1991), Nature, 353:90-94
Mary E. Knight et al. (1998), The Plant Journal 14(5), 613-622.
McElroy et al. (1990), Plant Cell, 2:163-171
Meijer et al. (1991), Plant Molecular Biology, 16:807-820
Ming Gao et al. (1997), Plant Physiol 114: 69-78.
Morris et al. (1992), Virology, 187:633
Muhitch M J. Et al., (1989) Plant Physiol. 1989 November; 91(3):868-875.
Mullis, K B (1987), Methods in Enzymology 155:335
Neuhaus et al., (1997)
Ohta et al. (1990), Plant Cell Physiology, 31:805
Poole et al., (1985), Cell, 40:37-43
Sambrook et al. (1989), Molecular Cloning, A Laboratory Manual, Cold Spring Harbour Laboratory Press p. 9.54-9.62
Santandrea G, et al., (2002), November; 50(4-5):743-56.
Schocher et al., (1986), BIOTECHNOLOGY, Vol 4; p 1093-1096.
Serna, A., et al., (2001). The Plant Journal, 25(6), pp. 687-698.
Siezen R. J., et al., (1995): In: Shinde U (ed). Intramolecular chaperones and folding. pp. 231-253. R.G. Landes Company. Austin Tex.
Snowdon et al. (1996), Plant Molecular Biology, 31:689
Taliercio E W, et al., (1999). J. Plant Physiol. Vol. 155 pp. 197-204.
Tanaka, H., et al., (2001). Development 128, pp 4681-4689.
Thomas W. G et al., (1998), The Plant Cell, Vol. 1295-1306.
Tornero, P., et al., (1996). Proc. Natl. Acad. Sci. June. Vol. 93, pp. 6332-6337.
Tornero, P., et al., (1997). The journal of biological chemistry. Vol. 272, No. 22, Issue of May 30, pp. 14412-14419.
Ujwal, S, and Masayori, I. (1996). Richard B., Christian B. (ed). Vol. 379, pp. 147-154. Plenum Press. New York.
Vancanneyt et al. (1990), Molecular and General Genetics, 220:245-250
Von Groll, U., et al., (2002). Plant Cell. Vol. 14, pp. 1527-1539.
Watson et al. (1994) Ed. De Boeck Université, pp 273-292.
White, J., et al., (1990) Nucl. Acid. Res. 18, 1062.
Wisniewski, J. P. y Rogowsky, P. (2004). Plant Molecular biology. Vol. 56, pp. 325-337.
Yoder et al., (1993) Biotechnology, 12, 263-292.
Zhang et al. (1995). Planta, 196: 84-94.
Zhou, A., et al., (1995). J. Biol. Chem. Vol. 270, pp. 21509-21516.

The invention claimed is:

1. An isolated nucleic acid molecule that has promoter activity specific to the pedicel and that comprises a DNA sequence selected from the group consisting of SEQ ID NO:1 and SEQ ID NO:2, wherein said isolated nucleic acid molecule is operatively linked to at least one heterologous nucleic acid sequence of interest.

2. An expression cassette comprising the nucleic acid molecule of claim 1.

3. The expression cassette according to claim 2, wherein said nucleic sequence of interest is selected from the group consisting of a sequence that encodes a peptide or a protein, a sequence antisense to a sequence encoding a polypeptide, a ribozyme sequence, and a RNAi sequence.

4. The expression cassette according to claim 2, in which the nucleic sequence of interest encodes a protein selected from the group consisting of a protein involved in development of the embryo and/or of the endosperm, a protein involved in determination of seed size and/or quality, a protein involved in cell growth, a protein involved in sugar or fatty acid metabolism, a protein involved in nutrient transfer and a protein improving resistance to a pathogen.

5. The expression cassette according to claim 2, which further comprises a selection marker gene for plants.

6. The expression cassette according to claim 2, wherein said nucleic sequence of interest is a gene encoding an invertase protein.

7. The expression cassette according to claim 2, wherein said nucleic sequence of interest is a gene encoding for a pathogen related peptide.

8. An expression vector containing at least an expression cassette according to claim 2.

9. A plant or bacterial host cell containing at least an expression cassette according to claim 2.

10. A transgenic plant, or a part of a transgenic plant, comprising a cell according to claim 9.

11. The plant or part of a plant according to claim 10, wherein said plant or part of plant is a cereal or oily plant.

12. The plant or part of a plant according to claim 11, which is from the group consisting of maize, rice, wheat, barley, rape, and sunflower.

13. A hybrid transgenic plant obtained by crossing a plant of claim 10.

14. A method of obtaining a plant having improved agronomic qualities and/or improved resistance to a pathogen, comprising:
(a) transforming at least one plant cell with at least an expression vector containing at least an expression cassette according to claim 2;
(b) cultivating the cell(s) thus transformed so as to generate a plant containing in its genome at least an expression cassette according to claim 2, whereby a plant having improved agronomic qualities and/or improved resistance to a pathogen is obtained.

* * * * *